(12) United States Patent
Winslow et al.

(10) Patent No.: US 10,617,774 B2
(45) Date of Patent: Apr. 14, 2020

(54) COVER WITH DISINFECTING ILLUMINATED SURFACE

(71) Applicant: Vital Vio, Inc., Troy, NY (US)

(72) Inventors: Cori Winslow, Ballston Spa, NY (US);
Colleen Costello, Yorktown Heights, NY (US); Nicholas Jones, Mechanicville, NY (US); Robert Barron, Port Washington, NY (US); William Grambo, Troy, NY (US); Jorel Lalicki, Troy, NY (US)

(73) Assignee: Vital Vio, Inc., Troy, NY (US)

( * ) Notice: Subject to any disclaimer, the term of this patent is extended or adjusted under 35 U.S.C. 154(b) by 0 days.

(21) Appl. No.: 16/000,690

(22) Filed: Jun. 5, 2018

(65) Prior Publication Data

US 2019/0167826 A1 Jun. 6, 2019

Related U.S. Application Data

(60) Provisional application No. 62/593,426, filed on Dec. 1, 2017, provisional application No. 62/593,474, filed on Dec. 1, 2017.

(51) Int. Cl.
*A61L 2/08* (2006.01)
*A61N 5/06* (2006.01)
(Continued)

(52) U.S. Cl.
CPC ............ *A61L 2/084* (2013.01); *A61N 5/0624* (2013.01); *F21V 3/02* (2013.01); *F21V 9/30* (2018.02);
(Continued)

(58) Field of Classification Search
CPC .................................. A61L 2/084; A61L 2/10
See application file for complete search history.

(56) References Cited

U.S. PATENT DOCUMENTS

| | | | |
|---|---|---|---|
| 1,493,820 A | 5/1924 | Miller et al. | |
| 2,622,409 A | 12/1952 | Stimkorb | |

(Continued)

FOREIGN PATENT DOCUMENTS

| | | | |
|---|---|---|---|
| CN | 201396611 Y | 2/2010 | |
| CN | 102213382 A | 10/2011 | |

(Continued)

OTHER PUBLICATIONS

Jappe, U., "Pathological mechanisms of acne with special emphasis on Propionibacterium acnes and related therapy," Acta Dermato-Venereologica, 2003, vol. 83, pp. 241-248.

(Continued)

*Primary Examiner* — Sean E Conley
(74) *Attorney, Agent, or Firm* — Banner & Witcoff, Ltd.

(57) ABSTRACT

A light emitting cover which inactivates microorganisms for covering a high touch surface is disclosed. The light emitting cover includes a body having an interior configured to cover at least a portion of the high touch surface and an exterior surface configured to be disinfected. At least an exterior portion of the body is transparent or translucent. A light emitter operably is coupled to the body for emitting a light through the exterior surface. The light exiting the exterior surface has at least a portion thereof having a wavelength in a range of 380 to 420 nanometers to disinfect the exterior surface.

20 Claims, 24 Drawing Sheets

(51) Int. Cl.

| | | |
|---|---|---|
| *F21V 33/00* | (2006.01) | |
| *F21V 29/70* | (2015.01) | |
| *F21V 9/30* | (2018.01) | |
| *F21V 3/02* | (2006.01) | |
| *F21V 15/015* | (2006.01) | |
| *F21V 23/00* | (2015.01) | |
| *B66B 31/02* | (2006.01) | |
| *F21Y 105/00* | (2016.01) | |
| *F21Y 115/20* | (2016.01) | |
| *F21Y 115/10* | (2016.01) | |
| *F21Y 115/15* | (2016.01) | |
| *A61L 2/24* | (2006.01) | |
| *E05B 1/00* | (2006.01) | |

(52) U.S. Cl.
CPC .......... *F21V 15/015* (2013.01); *F21V 23/003* (2013.01); *F21V 29/70* (2015.01); *F21V 33/006* (2013.01); *A61L 2/24* (2013.01); *A61L 2202/11* (2013.01); *A61L 2202/14* (2013.01); *A61N 2005/0626* (2013.01); *A61N 2005/0652* (2013.01); *A61N 2005/0653* (2013.01); *A61N 2005/0662* (2013.01); *B66B 31/02* (2013.01); *E05B 1/0069* (2013.01); *F21Y 2105/00* (2013.01); *F21Y 2115/10* (2016.08); *F21Y 2115/15* (2016.08); *F21Y 2115/20* (2016.08)

(56) References Cited

U.S. PATENT DOCUMENTS

| | | |
|---|---|---|
| 2,773,715 A | 12/1956 | Lindner |
| 3,314,746 A | 4/1967 | Millar |
| 3,670,193 A | 6/1972 | Horington et al. |
| 3,791,864 A | 2/1974 | Steingroever |
| 3,926,556 A | 12/1975 | Boucher |
| 3,992,646 A | 11/1976 | Corth |
| 4,121,107 A | 10/1978 | Bachmann |
| 4,461,977 A | 7/1984 | Pierpoint et al. |
| 4,576,436 A | 3/1986 | Daniel |
| 4,867,052 A | 9/1989 | Cipelletti |
| 4,892,712 A | 1/1990 | Robertson et al. |
| 4,910,942 A | 3/1990 | Dunn et al. |
| 5,231,472 A | 7/1993 | Marcus et al. |
| 5,489,827 A | 2/1996 | Xia |
| 5,530,322 A | 6/1996 | Ference et al. |
| 5,559,681 A | 9/1996 | Duarte |
| 5,668,446 A | 9/1997 | Baker |
| 5,721,471 A | 2/1998 | Begemann et al. |
| 5,725,148 A | 3/1998 | Hartman |
| 5,800,479 A | 9/1998 | Thiberg |
| 5,901,564 A | 5/1999 | Comeau, II |
| 5,962,989 A | 10/1999 | Baker |
| 6,031,958 A | 2/2000 | McGaffigan |
| 6,166,496 A | 12/2000 | Lys et al. |
| 6,183,500 B1 | 2/2001 | Kohler |
| 6,242,752 B1 | 6/2001 | Soma et al. |
| 6,246,169 B1 | 6/2001 | Pruvot |
| 6,251,127 B1 | 6/2001 | Biel |
| 6,379,022 B1 | 4/2002 | Amerson et al. |
| 6,477,853 B1 | 11/2002 | Khorram |
| 6,524,529 B1 | 2/2003 | Horton, III |
| 6,551,346 B2 | 4/2003 | Crossley |
| 6,554,439 B1 | 4/2003 | Teicher et al. |
| 6,627,730 B1 | 9/2003 | Burnie |
| 6,676,655 B2 | 1/2004 | McDaniel |
| 6,791,259 B1 | 9/2004 | Stokes et al. |
| 6,902,807 B1 | 6/2005 | Argoitia et al. |
| 7,015,636 B2 | 3/2006 | Bolta |
| 7,175,807 B1 | 2/2007 | Jones |
| 7,190,126 B1 | 3/2007 | Paton |
| 7,198,634 B2 | 4/2007 | Harth et al. |
| 7,201,767 B2 | 4/2007 | Bhullar |
| 7,213,941 B2 | 5/2007 | Sloan et al. |
| 7,438,719 B2 | 10/2008 | Chung et al. |
| 7,503,675 B2 | 3/2009 | Demarest et al. |
| 7,516,572 B2 | 4/2009 | Yang et al. |
| 7,521,875 B2 | 4/2009 | Maxik |
| 7,611,156 B2 | 11/2009 | Dunser |
| 7,612,492 B2 | 11/2009 | Lestician |
| 7,658,891 B1 | 2/2010 | Barnes |
| 7,955,695 B2 | 6/2011 | Argoitia |
| 8,035,320 B2 | 10/2011 | Sibert |
| 8,214,084 B2 | 7/2012 | Ivey et al. |
| 8,232,745 B2 | 7/2012 | Chemel et al. |
| 8,357,914 B1 | 1/2013 | Caldwell |
| 8,398,264 B2 | 3/2013 | Anderson et al. |
| 8,476,844 B2 | 7/2013 | Ancock et al. |
| 8,481,970 B2 | 7/2013 | Cooper et al. |
| 8,506,612 B2 | 8/2013 | Ashdown |
| 8,508,204 B2 | 8/2013 | Eurenberg et al. |
| 8,761,565 B1 | 6/2014 | Coleman et al. |
| 8,886,361 B1 | 11/2014 | Harmon et al. |
| 8,895,940 B2 | 11/2014 | Moskowitz et al. |
| 8,999,237 B2 | 4/2015 | Tumanov |
| 9,024,276 B2 | 5/2015 | Pugh et al. |
| 9,027,479 B2 | 5/2015 | Raksha et al. |
| 9,028,084 B2 | 5/2015 | Maeng et al. |
| 9,039,966 B2 | 5/2015 | Anderson et al. |
| 9,046,227 B2 | 6/2015 | David et al. |
| 9,078,306 B2 | 7/2015 | Mans et al. |
| 9,119,240 B2 | 8/2015 | Nagazoe |
| 9,173,276 B2 | 10/2015 | Van Der Veen et al. |
| 9,257,059 B2 | 2/2016 | Raksha et al. |
| 9,283,292 B2 | 3/2016 | Kretschmann |
| 9,313,860 B2 | 4/2016 | Wingren |
| 9,323,894 B2 | 4/2016 | Kiani |
| 9,333,274 B2 | 5/2016 | Peterson et al. |
| 9,368,695 B2 | 6/2016 | David et al. |
| 9,410,664 B2 | 8/2016 | Tames et al. |
| 9,420,671 B1 | 8/2016 | Sugimoto et al. |
| 9,433,051 B2 | 8/2016 | Snijder et al. |
| 9,439,271 B2 | 9/2016 | Ku et al. |
| 9,439,989 B2 | 9/2016 | Lalicki et al. |
| 9,492,576 B1 * | 11/2016 | Cudak ...................... A61L 2/10 |
| 9,581,310 B2 | 2/2017 | Wu et al. |
| 9,623,138 B2 | 4/2017 | Pagan et al. |
| 9,625,137 B2 | 4/2017 | Li et al. |
| 9,681,510 B2 | 6/2017 | van de Ven |
| 2002/0074559 A1 | 6/2002 | Dowling et al. |
| 2002/0122743 A1 | 9/2002 | Huang |
| 2003/0009158 A1 | 1/2003 | Perricone |
| 2003/0019222 A1 | 1/2003 | Takahashi et al. |
| 2003/0023284 A1 | 1/2003 | Gartstein et al. |
| 2003/0124023 A1 | 7/2003 | Burgess et al. |
| 2003/0178632 A1 | 9/2003 | Hohn et al. |
| 2003/0231485 A1 | 12/2003 | Chien |
| 2004/0008523 A1 | 1/2004 | Butler |
| 2004/0010299 A1 | 1/2004 | Tolkoff et al. |
| 2004/0024431 A1 | 2/2004 | Carlet |
| 2004/0039242 A1 | 2/2004 | Tolkoff et al. |
| 2004/0047142 A1 | 3/2004 | Goslee |
| 2004/0147984 A1 | 7/2004 | Altshuler et al. |
| 2004/0147986 A1 | 7/2004 | Baumgardner et al. |
| 2004/0158541 A1 | 8/2004 | Notarianni et al. |
| 2004/0159039 A1 | 8/2004 | Yates et al. |
| 2004/0162596 A1 | 8/2004 | Altshuler et al. |
| 2004/0230259 A1 | 11/2004 | Di Matteo |
| 2004/0262595 A1 | 12/2004 | Mears et al. |
| 2004/0266546 A1 | 12/2004 | Huang |
| 2005/0055070 A1 | 3/2005 | Jones et al. |
| 2005/0104059 A1 | 5/2005 | Friedman et al. |
| 2005/0107849 A1 | 5/2005 | Altshuler et al. |
| 2005/0107853 A1 | 5/2005 | Krespi et al. |
| 2005/0159795 A1 | 7/2005 | Savage et al. |
| 2005/0207159 A1 | 9/2005 | Maxik |
| 2005/0212397 A1 | 9/2005 | Murazaki et al. |
| 2005/0267233 A1 | 12/2005 | Joshi |
| 2006/0006678 A1 | 1/2006 | Herron |
| 2006/0009822 A1 | 1/2006 | Savage et al. |
| 2006/0022582 A1 | 2/2006 | Radkov |
| 2006/0071589 A1 | 4/2006 | Radkov |
| 2006/0085052 A1 | 4/2006 | Feuerstein et al. |

(56) References Cited

U.S. PATENT DOCUMENTS

| | | |
|---|---|---|
| 2006/0138435 A1 | 6/2006 | Tarsa et al. |
| 2006/0186377 A1 | 8/2006 | Takahashi et al. |
| 2006/0230576 A1 | 10/2006 | Meine |
| 2006/0247741 A1 | 11/2006 | Hsu et al. |
| 2006/0262545 A1 | 11/2006 | Piepgras et al. |
| 2007/0023710 A1 | 2/2007 | Tom et al. |
| 2007/0061050 A1 | 3/2007 | Hoffknecht |
| 2007/0115665 A1 | 5/2007 | Mueller et al. |
| 2007/0164232 A1 | 7/2007 | Rolleri et al. |
| 2007/0258851 A1 | 11/2007 | Fogg et al. |
| 2008/0008620 A1 | 1/2008 | Alexiadis |
| 2008/0015560 A1 | 1/2008 | Gowda et al. |
| 2008/0091250 A1 | 4/2008 | Powell |
| 2008/0278927 A1 | 11/2008 | Li et al. |
| 2008/0305004 A1 | 12/2008 | Anderson et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0285727 A1 | 11/2009 | Levy |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0107991 A1 | 5/2010 | Elrod et al. |
| 2010/0121420 A1 | 5/2010 | Fiset et al. |
| 2010/0148083 A1 | 6/2010 | Brown et al. |
| 2010/0179469 A1* | 7/2010 | Hammond ........... A61N 5/0603 604/20 |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Russell et al. |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1* | 10/2015 | Holub ..................... A61L 2/10 250/492.1 |
| 2016/0000950 A1 | 1/2016 | Won |
| 2016/0015840 A1 | 1/2016 | Gordon |
| 2016/0030610 A1 | 2/2016 | Peterson et al. |
| 2016/0091172 A1 | 3/2016 | Wu et al. |
| 2016/0114067 A1 | 4/2016 | Dobrinsky et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1* | 12/2016 | Rhodes ................ A61N 5/0624 |
| 2016/0354502 A1 | 12/2016 | Simmons et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0124883 A1 | 5/2018 | Bailey |
| 2018/0280723 A1 | 10/2018 | Enwemeka et al. |

FOREIGN PATENT DOCUMENTS

| | | |
|---|---|---|
| CN | 105304801 A | 2/2016 |
| CN | 205360038 U | 7/2016 |
| CN | 106937461 A | 7/2017 |
| DE | 102011001097 A1 | 9/2012 |
| DE | 102015207999 A1 | 11/2016 |
| EP | 0306301 A1 | 3/1989 |
| EP | 1693016 A1 | 8/2006 |
| EP | 1887298 A1 | 2/2008 |
| EP | 1943880 B1 | 4/2013 |
| FR | 2773715 A1 | 7/1999 |
| JP | 2003-332620 A | 11/2003 |
| JP | 2003339845 A | 12/2003 |
| JP | 2004261595 A | 9/2004 |
| JP | 2004275927 A | 10/2004 |
| JP | 2007511279 A | 5/2007 |
| JP | 2009-004351 A | 1/2009 |
| JP | 2011-513996 A | 4/2011 |
| JP | 2013-045896 A | 3/2013 |
| JP | 2013-093311 A | 5/2013 |
| JP | 2015-015106 A | 1/2015 |
| JP | 2015-035373 A | 2/2015 |
| KR | 20130096965 A | 9/2013 |
| KR | 101526261 B1 | 6/2015 |
| KR | 101648216 B1 | 8/2016 |
| KR | 20160127469 A | 11/2016 |
| KR | 101799538 B1 | 11/2017 |
| TW | M530654 U | 10/2016 |
| WO | 0114012 A1 | 3/2001 |
| WO | 03037504 A1 | 5/2003 |
| WO | 03063902 A2 | 8/2003 |
| WO | 03084601 A2 | 10/2003 |
| WO | 03089063 A1 | 10/2003 |
| WO | 2004033028 A2 | 4/2004 |
| WO | 2005048811 A2 | 6/2005 |
| WO | 2005049138 A1 | 6/2005 |
| WO | 2006023100 A1 | 3/2006 |
| WO | 2006100303 A2 | 9/2006 |
| WO | 2006126482 A1 | 11/2006 |
| WO | 2007012875 A1 | 2/2007 |
| WO | 2007035907 A2 | 3/2007 |
| WO | 2008071206 A1 | 6/2008 |
| WO | 2009056838 A1 | 5/2009 |
| WO | 2010110652 A1 | 9/2010 |
| WO | 2015066099 A2 | 5/2015 |
| WO | 2015189112 A1 | 12/2015 |
| WO | 2016019029 A1 | 2/2016 |
| WO | 2017009534 A1 | 1/2017 |
| WO | 2017205578 A1 | 11/2017 |

OTHER PUBLICATIONS

(56) References Cited

OTHER PUBLICATIONS

Burkhart, C. N. et al., "Assesment of etiologic agents in acne pathogenesis," Skinmed, 2003, vol. 2, No. 4, pp. 222-228.

Tong, Y., et al. "Population study of atmospheric bacteria at the Fengtai district of Beijing on two representative days," Aerobiologica, 1993, vol. 9, 1 page, Abstract only provided.

Tong, Y. et al., "Solar radiation is shown to select for pigmented bacteria in the ambient outdoor atmosphere," Photochemistry and Photobiology, 1997, val. 65, No. 1, pp. 103-106.

Marshall, J. H., et al., "Pigments of *Staphylococcus au reus*, a series of triterpenoid carotenoids," J. Bacteriology, 1981, vol. 147, No. 3, pp. 900-913.

Pelz, A. et al., "Structure and biosynthesis of staphyloxanthin production of methicillin-resistant *Staphylococcus aureus*," Biol. Pharm. Bull., 2012, val. 35, No. 1, 9 pages.

Sakai, K., et al., "Search for inhibitors of staphyloxanthin production by methicillin-resistant *Staphylococcus aureus*," Biol. Pharm. Bull., 2012, val. 35, No. 1, pp. 48-53.

Clauditz, A. et al., "Staphyloxanthin plays a role in the fitness of *Staphylococcus aureus* and its ability to cope with oxidative stress," Infection and Immunity, 2006, vol. 74, No. 8, 7 pages.

Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, http://www.jmest.org/wp-content/uploads/JMESTN42351112.pdf.

Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/.

Jun. 29, 2018—(DE) Office Action—App 112016003453.9.

Apr. 19, 2018—U.S. Non-Final Office Action—U.S. Appl. No. 15/886,366.

Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012.

Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 6 pages.

Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio. 3 pages.

International Search Report and Written Opinion issued in connection with corresponding PCT application PCT/US17/68749 dated Mar. 6, 2018.

International Search Report and Written Opinion for corresponding International Application No. PCT/US17/68755 dated Apr. 16, 2018, 17 pages.

Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE.

Berezow Alex, How to Kill Insects With Visible Light, Real Clear Science, Jan. 11, 2015, pp. 1-4, <https://www.realclearscience.com/journal_club/2015/01/12/how_to_kill_insects_with_visible_light_109021.html>.

Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan. <https://www.semanticscholar.org/paper/Lethal-effects-of-short-wavelength-visible-light-o-Hori-Shibuya/2c11cb3f70a059a051d8ed02fff0e8a9b7a4c4d4>.

Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>.

Jul. 19, 2018—U.S. Final Office Action—U.S. Appl. No. 15/856,971.
Oct. 1, 2018—U.S. Advisory Action—U.S. Appl. No. 15/856,971.
Jul. 17, 2018—U.S. Final Office Action—U.S. Appl. No. 15/857,128.
Oct. 1, 2018—U.S. Advisory Action—U.S. Appl. No. 15/857,128.
Sep. 21, 2018—U.S. Non-Final Office Action—U.S. Appl. No. 16/022,440.
Sep. 13, 2018—U.S. Non-Final Office Action—U.S. Appl. No. 15/940,127.
Nov. 1, 2018—U.S. Final Office Action—U.S. Appl. No. 15/886,366.
Dec. 3, 2018—U.S. Restriction Requirement—U.S. Appl. No. 15/856,971.
Dec. 3, 2018—U.S. Non-Final Office Action—U.S. Appl. No. 15/857,128.

Dornob, "Healthy Handle: Self-Sanitizing UV Dorr Knob Kils Germs", Dornob.com, Dec. 5, 2018, pp. 1-3, https://dornob.com/healthy-handle-self-sanitizing-uv-door-knob-kills-germs/.

Kickstarter, "Orb, The World's First Germ-Killing BLue/UV Light Ball", Dec. 10, 2018, pp. 1-10, <https://www.kickstarter.com/projects/572050089078660/orbtm-the-worlds-first-germ-killing-uv-light-ball>.

Nutone, "QTNLEDB LunAura Collection 110 CFM Fan,Light,LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809.

Nutone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90.

Nutone, "Ultra Pro™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca.

Dai et al., "Blue light for infectious diseases: Propionibacterium acnes, Helicobacter pylon, and beyond?," Drug Resist Update, 15(4): 223-236 {Aug. 2012).

Halstead et al., "The antibacterial activity of blue light against nosocomial wound pathogens growing planktonically and as mature biofilms," Appl. Environ, Microbial., Apr. 2016, 38 pages, retrieved from: http://aem.asm.org/.

R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214.

Tomb et al., "Inactivation of Streptomyces phage C31 by 405 nm light," Bacteriophage, 4:3, Jul. 2014, retrieved from: http://dx.doi.org/10.4161/bact.32129, 7 pages.

Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://lwww.researchgate.net/publication/304628914.

International Search Report and Written Opinion issued in connection with corresponding PCT Application No. PCT/US2016/036704 dated Dec. 8, 2016, 20 pages.

LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html, Published Jun. 14, 2007, 2 pages.

LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.

LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.

LEDs Magazine, "ANSI continues advancements on SSL chromaticity standard," retrieved from the Internet on Apr. 20, 2017 at: http://lwww.ledsmagazine.com/articles/print/volume-12/issue-11/features/standards/ansi-continues-advancements-on-ssl-chromaticity-standard.html, Published Dec. 8, 2015, 6 pages.

(56) References Cited

OTHER PUBLICATIONS

Soraa, "PAR30L," retrieved from the Internet on Apr. 20, 2017 at: http://www_soraa.com/products/22-PAR30L, 6 pages.

Soraa, "PAR30L 18.5W," retrieved from the Internet on Apr. 20, 2017 at: http://www.soraa.com/products, 5 pages.

Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76.

Patent Cooperation Treaty, Search Report—Written Opinion, International Application No. PCT/US16/44634, dated Oct. 20, 2016, 14 pages.

Color Phenomena, "CIE-1931 Chromaticity Diagram," last updated Aug. 22, 2013, retrieved from www.color-theory-phenomena.nl/10.02.htm on Jan. 20, 2016, 3 pages.

Patent Cooperation Treaty, Written Opinion of the International Searching Authority and International Search Report for PCT/US2015/042678 dated Nov. 20, 2015, 13 pages.

Patent Cooperation Treaty, International Preliminary Report on Patentability for PCT/GB2008/003679 dated May 4, 2010, 9 pages.

Patent Cooperation Treaty, Written Opinion of the International Searching Authority and International Search Report for PCT/GB2008/003679 dated Oct. 31, 2008, 11 pages.

U.S. Appl. No. 15/886,420, Office Action dated May 9, 2018, 9 pages.

U.S. Appl. No. 15/223,134, Third Party Submission submitted Jun. 6, 2017, 25 pages.

Yi, Notice of Allowance and Fee(s) due for U.S. Appl. No. 14/501,931 dated Jan. 20, 2016, 8 pages.

Yu, J. et al., "Efficient Visible-Light-Induced Photocatalytic Disinfection on Sulfur-Doped Nanocrystalline Titania," Environ. Sic. Technol., 39, 2005, pp. 1175-1179.

Demidova, T. et al., "Photodynamic Therapy Targeted to Pathogens," International Journal of Immunipathology and Pharmacology, 17(3), pp. 245-254.

Ashkenazi, H. et al., "Eradication of Propionibacterium acnes by its endogenic porphyrins after illumination with high intensity blue light," FEMS Immunology and Medical Microbiology, 35, pp. 17-24.

Elman, M. et al., "The Effective Treatment of Acne Vulgaris by a High-intensity, Narrow Band 405-420 nm Light Source," Cosmetic & Laser Ther, 5, pp. 111-116.

Sikora, A. et al., "Lethality of visable light for *Escherichia coli*hemH 1 mutants influence of defects in DNA repair," DNA Repair, 2, pp. 61-71.

Huffman, D. et al., "Inactivation of Bacteria, Virus and Cryptospordium by a Point-of-use Device Using Pulsed Broad Spectrum White Light," Wat. Res. 34(9), pp. 2491-2498.

Papageorgiou, P. et al., "Phototherapy with Blue (415 nm) and Red (660 nm) Light in the Treatment of Acne Vulgaris," British Journal of Dermatology, 2000, pp. 973-978.

Burchard, R. et al., "Action Spectrum for Carotenogenesis in Myxococcus xanthus," Journal of Bateriology, 97(3), 1969, pp. 1165-1168.

Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.

Yoshimura et al., "Antimicrobial effects of phototherapy and photochemotherapy in vivo and in vitro," British Journal of Dermatology, 1996, 135: 528-532.

Wilson et al., "Killing of methicillin-resistant *Staphylococcus aureus* by low-power laser light," J. Med, Microbial., vol. 42 (1995), pp. 62-66.

Kawada et al., "Acne Phototherapy with a high-intensity, enhanced, narrow-band, blue light source: an open study and in vitro investigation," Journal of Dermatological Science 30 (2002) pp. 129-135.

Maclean et al., "High-intensity narrow-spectrum light inactivation and wavelength sensitivity of *Staphylococcus auresu*," FEMS Microbial. Lett., vol. 285 (2008) pp. 227-232.

Reed, "The History of Ultraviolet Germicidal Irradiation for Air Disinfection," Public Health Reports, Jan.-Feb. 2010, vol. 125, 13 pages.

Ward, "Experiments on the Action of Light on Bacillus anthracis," Received Dec. 15, 1892, 10 pages.

Hamblin et al., "Helicobacter pylori Accumulates Photoactive Porphyrins and Is Killed by Visable Light," Antimicrobial Agents and Chemotherapy, Jul. 2005, pp. 2822-2827.

Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3}, pp. 1238-1245.

Holzman, "405-nm Light Proves Potent at Decontaminating Bacterial Pathogens," retrieved from: http://forms.asm.org/microbe/index.asp?bid=64254 on Aug. 6, 2015, 34 pages.

Guffey et al., "In Vitro Bactericidal Effects of 405-nm and 470-nm Blue Light," Photomedicine and Laser Surgery, vol. 24, No. 6, retrieved from: https://lwww.liebertpub.com/doi/abs/10.1089/pho.2006.24.684 on Mar. 23, 2018, 2 pages, abstract only provided.

Kristoff et al., "Loss of photoreversibility for UV mutation in *E. coli* using 405 nm or near-US challenge," Mutat Res., May 1983, 109{2}: 143-153, 2 pages, abstract only provided.

Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, Aug. 1981, pp. 410-417.

Knowles et al., "Near-Ultraviolet Mutagenesis in Superoxide Dismutase-deficient Strains of *Escherichia coli*," Environmental Health Perspectives, vol. 102{1}, Jan. 1994, pp. 88-94.

Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.

Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.

Bek-Thomsen, M., "Acne is Not Associated with Yet-Uncultured Bacteria," J. Clinical Microbial., 2008, 46{10), 9 pages.

Harrison, A.P., "Survival of Bacteria," Annu. Rev. Microbial, 1967, p. 143, vol. 21.

Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only.

Pochi, P.E., "Acne: Androgens and microbiology," Drug Dev, Res., 1988, val. 13, 4 pages, abstract only provided.

Burkhart, C. G. et al., "Acne: a review of immunologic and microbiologic factors," Postgraduate Medical Journal, 1999, vol. 75, pp. 328-331.

Nutone, "NuTone Bath and Ventilation Fans", Dec. 11, 2018, pp. 1-2, http://www.nutone.com/products/filter/qt-series-fanlights-25a05450-d47b-4ab8-9992-f8c2cd3f71390.

Dec. 12, 2018—U.S. Final Office Action—U.S. Appl. No. 15/886,420.

Nov. 27, 2018—Japanese Office Action—JP 2018-525520.

Jan. 9, 2019—U.S. Notice of Allowance amd Fee(s) Due—U.S. Appl. No. 15/940,127.

Jan. 4, 2019—Taiwan Office Action—ROC (Taiwan) Pat. Appl. No. 104124977.

Feb. 11, 2019—(WO) International Search Report—App PCT/US2018/061859.

Feb. 28, 2019—(WO) International Search Report—App PCT/US2018/061843.

Feb. 28, 2019—(WO) International Search Report—App PCT/US2018/061856.

Apr. 5, 2019—U.S. Non-Final Office Action—U.S. Appl. No. 15/886,420.

Apr. 15, 2019—(CA) Examiner's Report—App 2,993,825.

May 1, 2019—U.S. Notice of Allowance—U.S. Appl. No. 15/940,127.

May 29, 2019—U.S. Non-Final Office Action—U.S. Appl. No. 16/000,426.

(56) References Cited

OTHER PUBLICATIONS

May 24, 2019—U.S. Final Office Action—U.S. Appl. No. 16/000,690.
Jun. 20, 2019—U.S. Final Office Action—U.S. Appl. No. 15/857,128.
Jun. 5, 2019—U.S. Non-Final Office Action—U.S. Appl. No. 16/369,484.
Absorption and Fluorescence Spectroscopy of Tetraphenylporphyrin§ and Metallo-Tetraphenylporphyrin, article, 2005, 11 pp., Atomic, Molecular and Supramolecular Studies.
Dayer, et al., Band Assignment in Hemoglobin Porphyrin Ring Spectrum: Using Four-Orbital Model of Gouterman, article, Sep. 8, 2009, 7 pp., Protein & Peptide Letters, 2010, vol. 17, No. 4, Department of Biology, Faculty of Sciences, Shahid Chamran University of Ahvaz, Tehran, Iran.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2 , 2017, J Fac Med Baghdad.
Nussbaum, et al., Effects of 630-, 660-, 810-, and 905-nm Laser Irradiation, Delivering Radiant Exposure of 1-50 J/cm2 on Three Species of Bacteria in Vitro, journal, 2002, 9 pp., vol. 20, No. 6, 2002, Journal of Clinical LaserMedicine & Surgery, Canada.
Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea.
Rita Giovannetti, The Use of Spectrophotometry UV-Vis for the Study of Porphyrins, article, 2012, 23 pp., InTech Europe, Croatia.
Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University Of Hull, Kingston-Upon-Hull, HU6 7RX, U. K.
Jul. 8, 2019—(WO) ISR & WO—App PCT/US2019/024593.
Aug. 1, 2019—U.S. Final Office Action—U.S. Appl. No. 15/856,971 (no refs).

\* cited by examiner

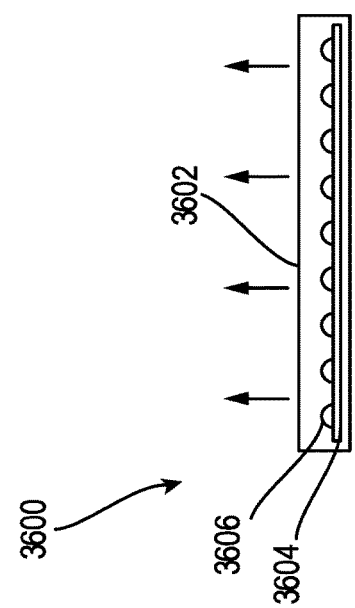
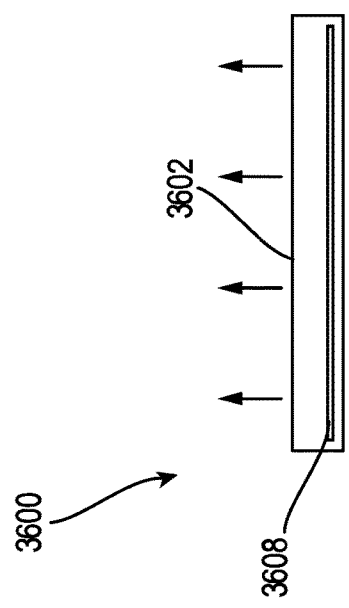
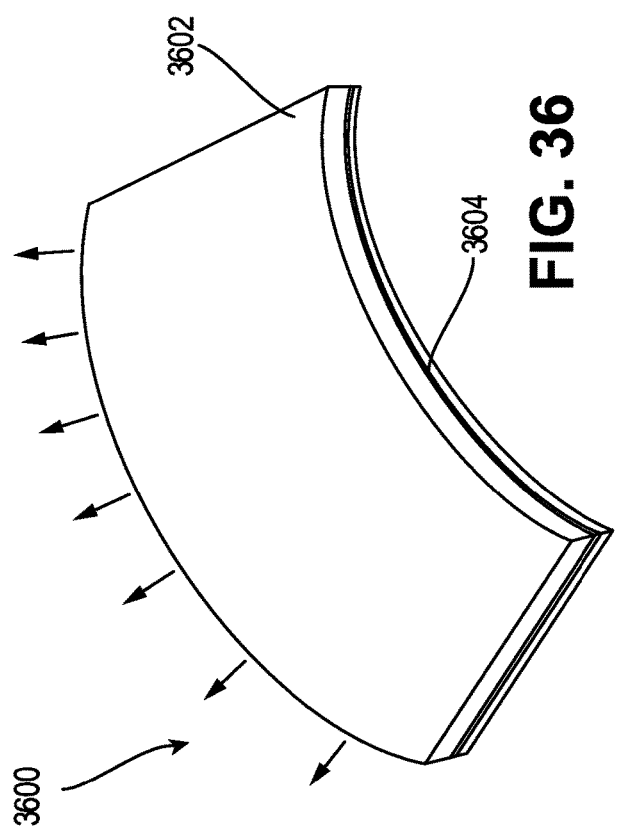
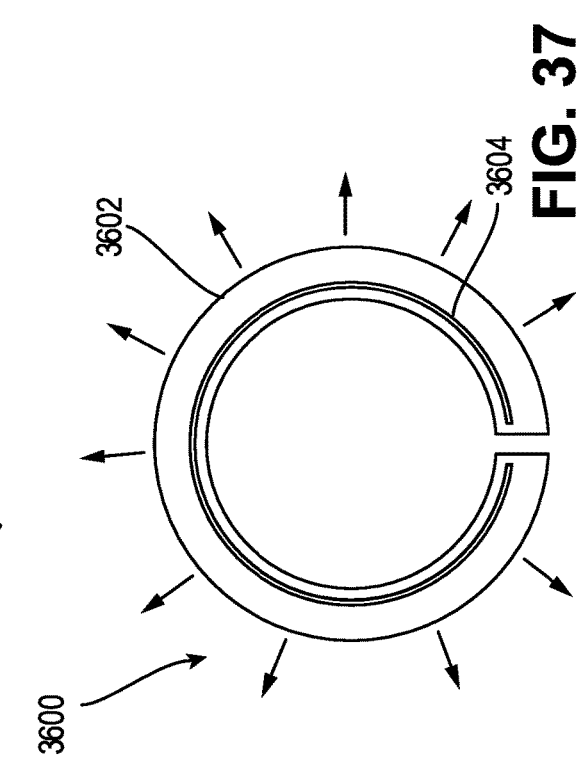

COVER WITH DISINFECTING ILLUMINATED SURFACE

CROSS REFERENCE TO RELATED APPLICATIONS

This patent claims the benefit of U.S. Provisional Patent Application No. 62/593,474 filed Dec. 1, 2017 and entitled "DEVICES USING FLEXIBLE LIGHT EMITTING LAYER FOR CREATING DISINFECTING ILLUMINATED SURFACE, AND RELATED METHOD," and U.S. Provisional Patent Application No. 62/593,426 filed Dec. 1, 2017 and entitled "COVER WITH DISINFECTING ILLUMINATED SURFACE." U.S. Provisional Patent Application No. 62/593,474 and U.S. Provisional Patent Application No. 62/593,426 are hereby incorporated herein by reference in their entireties.

TECHNICAL FIELD

The present disclosure relates to surface disinfection, and more specifically, to a cover with a disinfecting illuminated surface.

BACKGROUND

Touch surfaces, particularly, high touch surfaces, are commonly inhabited by harmful microorganisms due to the nature of their use by humans or other animals. Microorganisms transfer from, e.g., human to human, through contact of the same high touch surfaces and can cause illness to the users. Harmful bacteria such as *Escherichia coli* (*E. coli*), *Salmonella*, Methicillin-resistant *Staphylococcus Aureus* (MRSA), and *Clostridium Difficile* can be found on many surfaces, increasing the chance of a user becoming sick or transmitting the bacteria. For example, there are numerous cases of hospital acquired infections due to bacteria such as the ones mentioned previously that cause unnecessary illness and money spent towards medical care. Healthcare facilities are not the only ones at risk for causing illness. For example, athletic facilities/gyms, public transportation vehicles, food preparation or production plants, hotels, offices, etc., are all at risk for hosting the contraction of bacterial related illnesses by their inhabitants.

SUMMARY

Systems, methods, and apparatuses of the present disclosure relate to light emitting covers to be retrofitted onto various high touch surfaces. In some examples, the light emitting cover inactivates microorganisms on a transparent or translucent body (which may be flexible) with a light emitter disposed therein. The light emitter may emit a light through the exterior surface at or around a wavelength range, e.g., 380 to 420 nanometers, and with minimum irradiance sufficient to initiate inactivation of microorganisms.

The foregoing and other features of the disclosure will be apparent from the following more particular description of embodiments of the disclosure.

BRIEF DESCRIPTION OF THE DRAWINGS

Examples herein will be described in detail, with reference to the following figures, wherein like designations denote like elements, and wherein:

FIGS. 36-39 show various views of a flexible device and/or cover according to systems, methods, and apparatuses of the present disclosure.

It is noted that the drawings of the disclosure are not to scale. The drawings should not be considered as limiting the scope of the disclosure. In the drawings, like numbering represents like elements.

DETAILED DESCRIPTION

Figure 1:
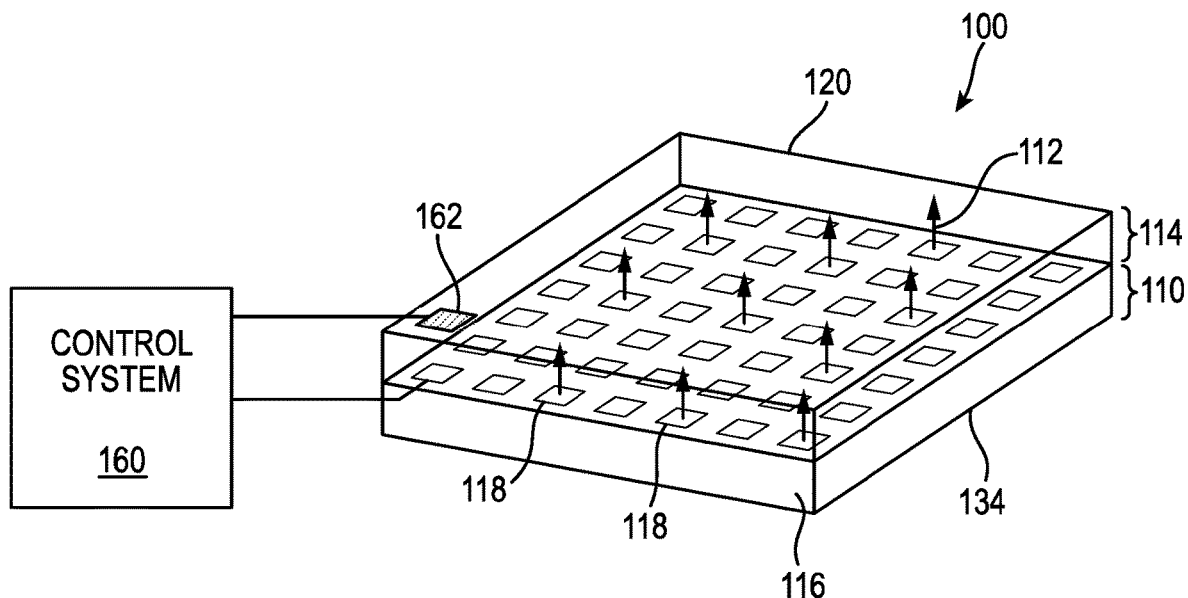
FIG. 1 shows a perspective view of a light emitting device and/or cover according to systems, methods, and apparatuses of the present disclosure.

High touch surfaces, such as handles, are conventionally disinfected in a number of ways. The most common technique is cleaning with disinfecting, chemical cleaners. Challenges with chemical cleaners are that they provide only intermittent disinfection, and allow the buildup of harmful microorganisms between cleanings. Since humans may touch high touch surfaces at any time, continuous disinfection is desired.

Another approach employs antimicrobial coatings such as silver, copper or zinc, to disinfect. These coatings may be applied directly to surfaces, or may be provided in handles that cover high touch surfaces. These coatings may wear off or may require replenishing, and thus may have a limited lifetime. They may also be unsafe for human or internal contact, and may be messy to use. Antimicrobial coatings may also damage surfaces to which they are applied. Another approach employs single use, disposable layers on high touch surfaces. These disposable layers cause unnecessary waste and require user interaction for them to be effective.

Another approach to disinfect high touch surfaces employs disinfecting, internal illumination systems that transmit ultraviolet (UV) light through a high touch surface. UV light is harmful to humans, so the light must be off during human use. Accordingly, these systems typically require complex controls to prevent harmful, direct exposure to humans.

Many products exist that illuminate an enclosed area with disinfecting wavelengths of light, usually UV, thus disinfecting any object placed inside the enclosed area. Objects such as dental devices, electronics, pacifiers, sports equipment, etc., may be disinfected using this method. Enclosed disinfection only provides intermittent disinfection. The object placed within the disinfecting light enclosure is disinfected for the period of time it is exposed, but as soon as it exits and comes back into contact with a user, it is susceptible to harboring bacteria and spreading illness. If the enclosed disinfection is performed with ultraviolet light on an object containing plastic, there is the possibility the plastic may be degraded. Other products are available that illuminate entire rooms to disinfect as part of general illumination systems, e.g., using controlled UV light or white light with a certain proportion of disinfecting light therein. These systems may be inadequate for a high touch surface that is not in a location capable of or configured for being exposed to general illumination.

Other challenges for providing disinfection to high touch surfaces include creating a disinfection system for surfaces having irregular shapes, or for pre-existing surfaces and/or objects not originally intended to have such a disinfection system associated therewith.

Systems, methods, and apparatuses described herein provide a light emitting device and/or cover which inactivates microorganisms, and may be used to create or cover a high touch surface. An example light emitting device may include a flexible light emitting layer emitting a light; and a transparent or translucent layer over the flexible light emitting layer. The light travels through and exits an exterior surface of the transparent or translucent layer, creating an exiting light. At least a portion of the exiting light exiting the transparent or translucent layer may have a wavelength in a range of 380 to 420 nanometers (nm) e.g., 405 nm, and may disinfect the exterior surface of the transparent or translucent layer. The light emitting device may be used alone to create a self-disinfecting high touch surface, e.g., on a door, or may be shaped to mate with other structures to create a disinfecting high touch surface, e.g., a rigid transparent conduit. A method of producing the light emitting device is also described herein.

An example light emitting cover may include a body having an interior configured to cover at least a portion of the high touch surface and an exterior surface configured to be disinfected. The exterior surface of the cover replaces the high touch surface. At least an exterior portion of the body is transparent or translucent such that light may travel therethrough to the exterior, touch surface. A light emitter is operably coupled to the body for emitting a light through the exterior surface. In contrast to conventional systems that employ ultraviolet (UV) light, at least a portion of the light exiting the exterior surface may have a wavelength in a range of 380 to 420 nanometers (nm), e.g., 405 nm, and may disinfect the exterior surface.

The wavelengths described above may inactivate microorganisms such as but not limited to: *Escherichia coli* (*E. coli*), *Salmonella*, Methicillin-resistant *Staphylococcus Aureus* (MRSA), *Clostridium Difficile*, and a wide variety of yeasts and/or fungi.

Figure 2:
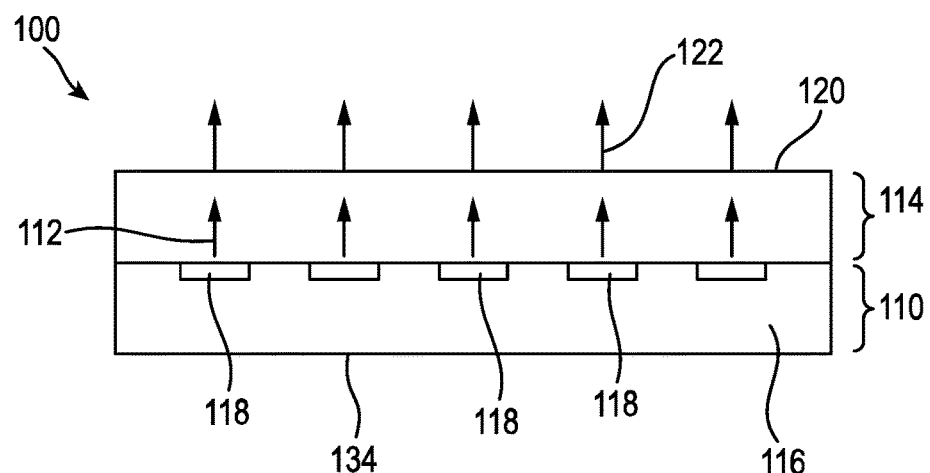
FIG. 2 shows a side view of a light emitting device according to systems, methods, and apparatuses of the present disclosure.

Referring to the drawings, examples of a light emitting device which inactivates microorganisms are illustrated. FIG. 1 shows a perspective view, and FIG. 2 shows a side view, of one example light emitting device 100 (hereinafter "device 100"). Device 100 may generally include a flexible light emitting layer 110 emitting a light 112, and a transparent or translucent layer 114 over flexible light emitting layer 110. Flexible light emitting layer 110 may include any now known or later developed light emitting element(s) capable of being flexed or bent into a desired position. In some examples, such as that shown in FIG. 2, flexible light emitter 112 may include a flexible substrate 116 and one or more light emitting elements 118 therein or thereon. Flexible substrate 116 may include, for example, a flexible printed circuit board including the one or more discrete light emitters 118 thereon. Each light emitting element 118 may include an LED(s). Where desired, each light emitting element 118 may include a flexible LED(s). In some examples, flexible light emitter 110 may include an electroluminescent panel, and in some examples, flexible light emitter 110 may include an organic light emitting diode (OLED) layer. Flexible light emitting layer 110 may include any number of actual emitters necessary to disinfect exterior surface 120 and create the desired color, intensity, irradiance, etc.

Figure 3A:
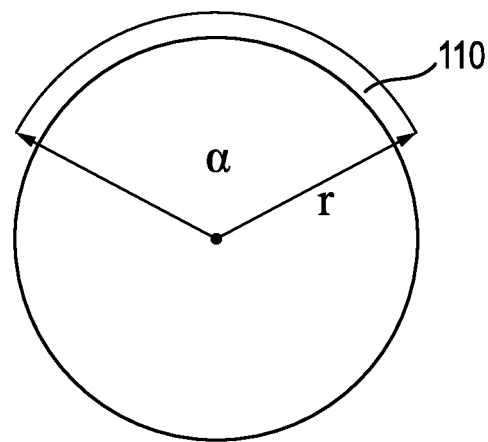
FIG. 3A shows a side view of a light emitting device and/or cover and its degree of flexibility according to systems, methods, and apparatuses of the present disclosure.

Transparent or translucent layer 114 (hereinafter "TT layer 114") is positioned over flexible light emitting layer 110. That is, TT layer 114 is coupled over and to flexible light emitting layer 110. As used herein, "transparent" or "translucent" may indicate any level of light transmission short of opaque. As shown in FIGS. 1 and 2, flexible light emitting layer 110 may be flush to TT layer 114, e.g., surface to surface. Light 112 from light emitting layer 110 may travel through and exit an exterior surface 120 of TT layer 114, creating an exiting light 122. A portion of exterior surface 120 (not shown) may not be transparent or translucent. As used herein, "flexible" may indicate a capability of being formed into alternative shapes, e.g., forming, from a flat original shape, an arc having a minimum angle α of approximately 120 degrees and a minimum bend radius (r) of approximately 0.3 inches bent on any axis falling on the plane of the flexible light emitter for handle applications (see FIG. 3A). A larger radius of flexibility may be sufficient for non-handle applications, e.g., a bend radius of 1.0 inches. Other levels of flexibility may also be possible depending on application.

At least a portion of the exiting light 122 (arrows) exiting TT layer 114 may have a wavelength in a range of approximately 380 to approximately 420 nanometers (nm). This wavelength of light may inactivate microorganisms such as but not limited to: *Escherichia coli* (*E. coli*), *Salmonella*, Methicillin-resistant *Staphylococcus Aureus* (MRSA), *Clostridium Difficile*, and a wide variety of yeasts and/or fungi. In some examples, exiting light 122 may have at least a portion thereof at a wavelength of 405 nm. Exiting light 122 may disinfect exterior surface 120 of TT layer 114. Exiting light 122 may have any irradiance or intensity sufficient to disinfect exterior surface 120, which may vary depending on, for example: the type of material of TT layer 114, the level of microorganisms thereon, the extent of touching (e.g., low level bedroom door handle versus high level grocery cart handle), the type of application, etc.

In some examples, disinfecting light includes light with a disinfecting dosage sufficient to stop, decrease, impede, or eliminate bacteria and/or bacteria population growth. In some examples, the disinfecting dosage may be characterized in terms of irradiance or instantaneous energy with units such as, for example, milliwatts per centimeter squared (mW/cm$^2$). In some such examples, the disinfecting dosage may have a minimum irradiance threshold at or around 0.01 mW/cm$^2$. In some examples, the disinfecting dosage may be characterized in terms of radiant exposure with units such as, for example, Joules per centimeter squared (J/cm$^2$).

In some examples, exiting light 122 may have an irradiance of at least 0.01 or 0.02 mW/cm$^2$, e.g., from all or at least part of exterior surface 120. Light 112 emitted from flexible light emitting layer 110 and/or exiting light 122 may have any color desired, so long as sufficient light to disinfect in the 380-420 nm range is present therein. As will be described herein, exiting light 122 may be solely between 380 to 420 nm wavelength light. Alternatively, exiting light 122 may include or be converted to include at least one additional portion of light above 420 nanometers to create disinfecting light of another color, such as white light.

Flexible light emitting layer 110 may emit light 112 that is the same as exiting light 122 that exits exterior surface 120 of TT layer 114 (e.g., the TT layer 114 may not change the wavelength of light 112). In one example, exiting light 122 may include light exclusively in the range of 380 to 420 nanometers. Alternatively, flexible light emitting layer 110 may be controlled to emit a variety of other different wavelengths and colors, but including some portion that is in the range of 380 to 420 nanometers sufficient to disinfect exterior surface 120. Any color or intensity may be achieved in this manner, e.g., to match a color of a structure to which device is attached.

In some examples, light 112 may be converted at some point during its travel prior to exiting exterior surface 120 as exiting light 122 to create disinfecting light of another color such as white light. For example, light 112 may be converted to a white light having a portion thereof with the wavelength in the range of 380 to 420 nanometers, but also other wavelengths of light, e.g., 450-500 nm and 550-700 nm, to create the white light. For example, 450-500 nm light may be produced using blue phosphors and 550-700 nm light may be produced using nitride phosphors. Other colors of light may also be generated in this manner.

Figure 3B:
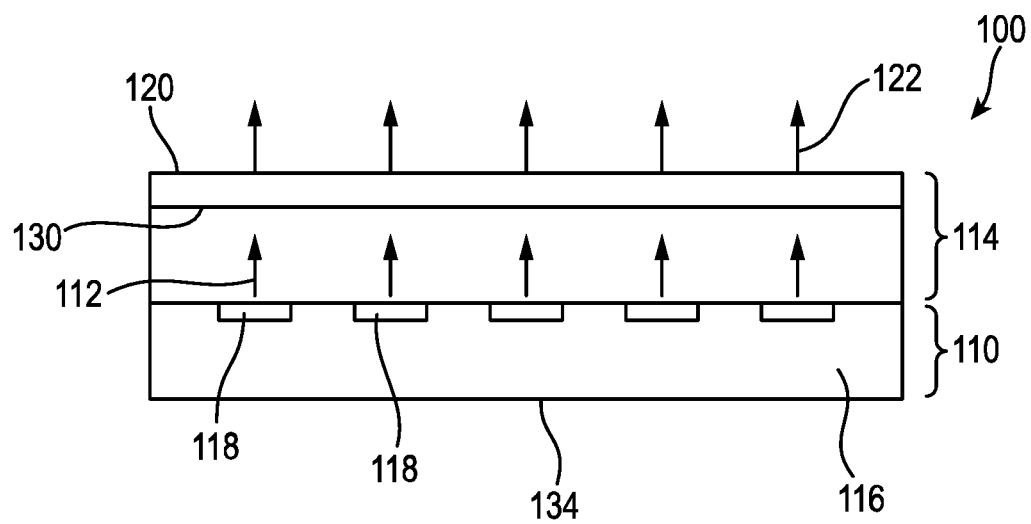
FIG. 3B shows a side view of a light emitting device and/or cover including a light-converting layer according to systems, methods, and apparatuses of the present disclosure.

In the illustrated example of FIG. 3B, TT layer 114 may include a light-converting layer(s) 130 through which light 112 may travel to convert another portion of light 112 to a wavelength(s) different from the wavelength of light 112 emitted from flexible light emitting layer 110. In some examples, the light-converting layer 130 may be embedded in TT layer 114 near exterior surface 120. In some examples, the light-converting 130 may be an additional layer over or under the TT layer 114. The light-converting layer 130 may be located anywhere along a path of light 112. Light-converting layer 130 may include any now known or later developed layer(s) for converting all or certain portion(s) of light 112 to different wavelengths. In some examples, light-converting layer 130 may include at least one phosphor, at least one optical brightener and/or at least one quantum dot. Light-converting layer 130 may tune light 122 to, for example, alter a color tint of exterior surface 120 or the color tint of the material directly surrounding each of light emitters 118, etc., internal to device 100. Light-converting layer 130 may be segmented across the layer's surface to convert light 112 to two or more different wavelengths, e.g., one segment to allow some of light 112 to pass unconverted, another segment to convert some of light 112 to another wavelength, and another segment to convert some of light 112 to yet another wavelength. In any event, exiting light 122 may be customized to provide disinfection and a desired color. In one non-limiting example, exiting light 122 may have a color rendering index (CRI) value of at least 70, a correlated color temperature (CCT) between approximately 2,500 K and 5,000 K and/or a proportion of spectral energy measured in the 380 nm to 420 nm wavelength range, wherein the proportion of spectral energy may range between 10% and 44%.

Figure 4:
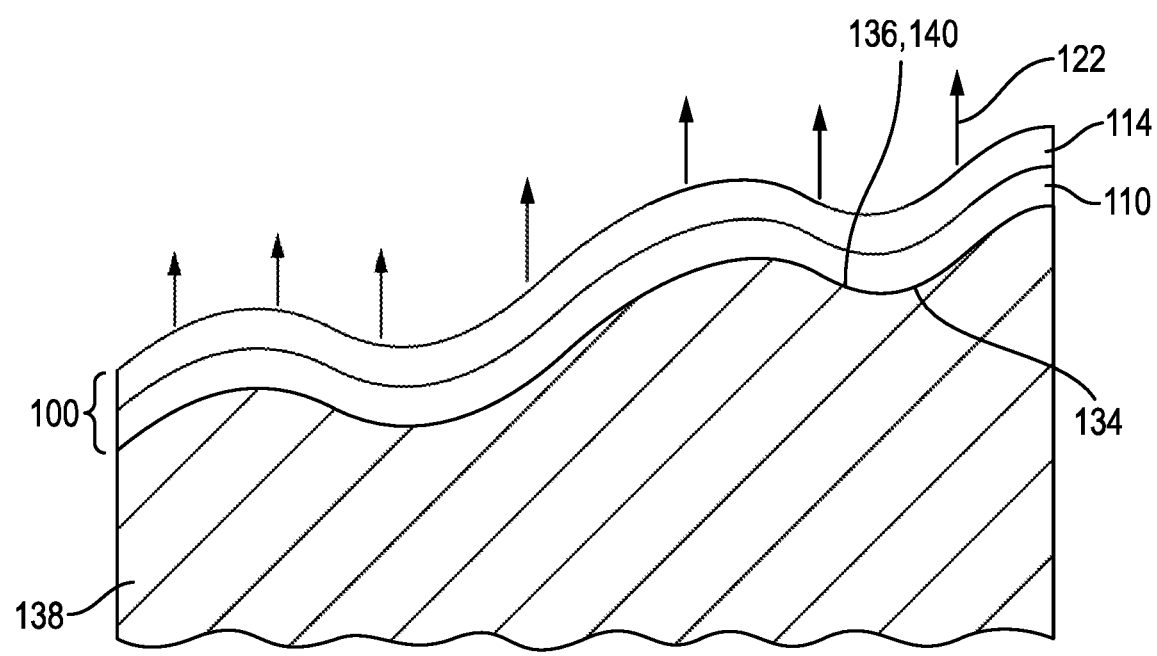
FIG. 4 shows a side view of a light emitting device and/or cover on an irregular shape according to systems, methods, and apparatuses of the present disclosure.

As further described herein, device 100 may be used to cover at least a portion of a high touch surface of a structure. The type of structure to which it may be applied may be based, at least in part, on the form of TT layer 114. In some examples, TT layer 114 may be flexible. TT layer 114 may include any now known or later developed flexible transparent or translucent material such as a clear plastic, rubber, flexible glass, etc. Device 100 may be applied to any touch surface regardless of surface shape thereof. Device 100 may be flexed or bent to cover any irregularly shaped surface. Device 100 may include a back surface 134 on flexible light emitting layer 110. The back surface 134 may be coupled to a high touch surface 136 via adhesive, fasteners, or other mechanically coupling features. Structure 138 may include high touch surface 136 and may be practically any object, surface, or thing. In the illustrated example of FIG. 4 device 100 may be shaped to comport with the shape of a surface 140 of structure 138 to which it is attached. Other example structures 138 for which device 100 alone may be beneficial may include any sort of handle grasped by users, e.g., a door handle, refrigerator handle, etc. Device 100 may be wrapped around, for example, a rounded (e.g., ovular, circular, etc.) structure. Because exterior surface 120 of TT layer 114 may be configured to be disinfected by exiting light 122, device 100 may provide a disinfected high touch surface replacement. That is, exterior surface 120 may replace high touch surface 136 as the outside part or layer of structure 138 to which device 100 is coupled.

Figure 5:
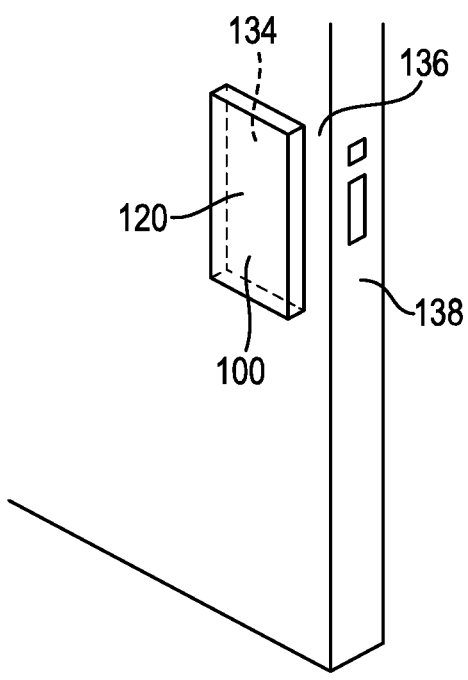
FIG. 5 shows a perspective view of a light emitting device and/or cover on a door according to systems, methods, and apparatuses of the present disclosure.
Figure 6:
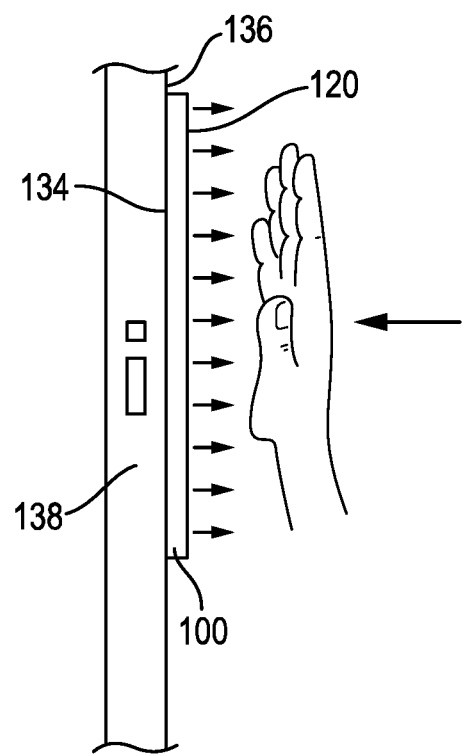
FIG. 6 shows a side view of the light emitting device and/or cover of FIG. 5.
Figure 7:
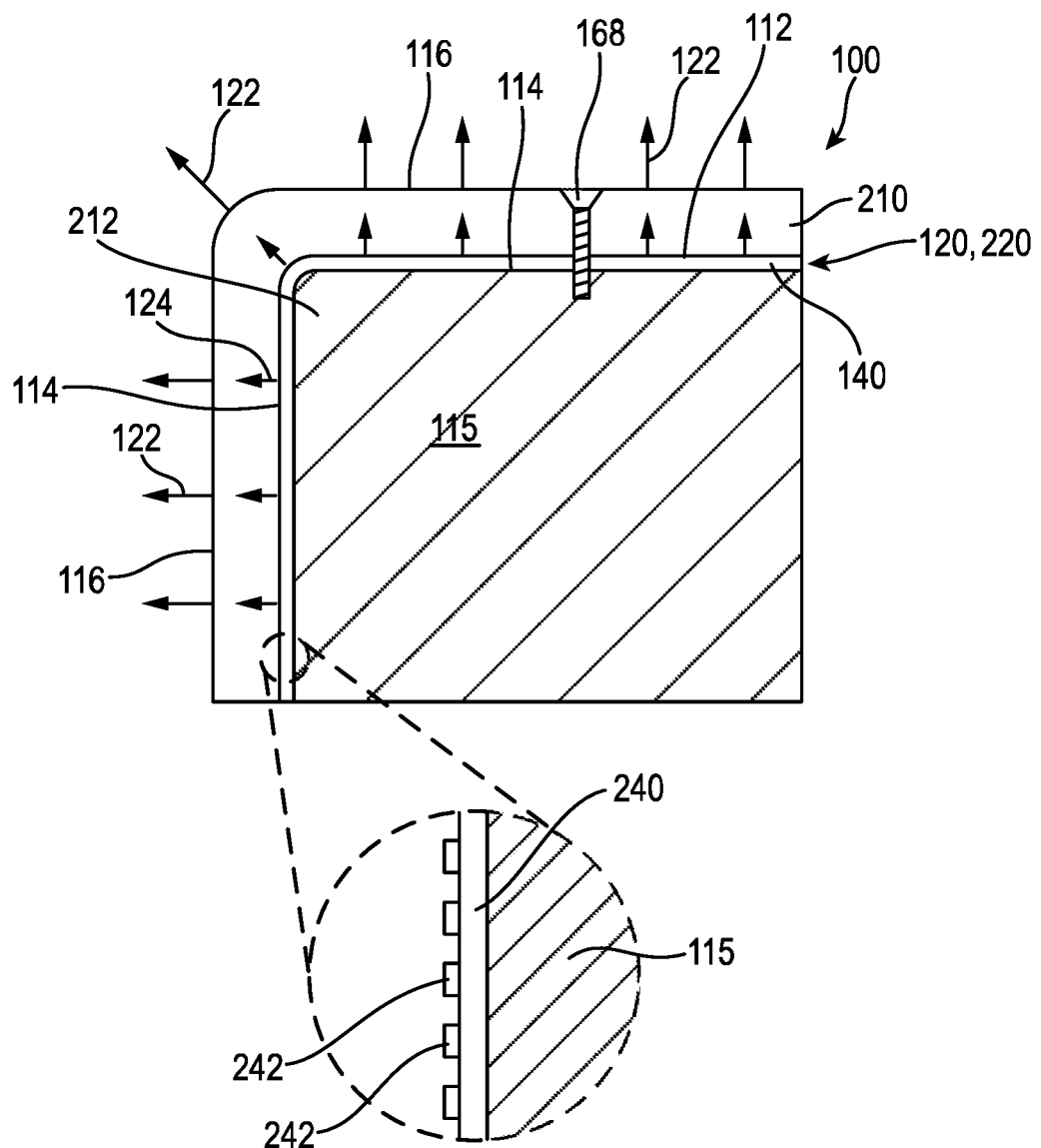
FIG. 7 shows a cross-sectional view of a light emitting device and/or cover according to systems, methods, and apparatuses of the present disclosure.

Referring to FIGS. 5 and 6, another example device 100 covering at least a portion of a high touch surface 136 of structure 138, is shown. In FIGS. 5 and 6, structure 138 may include a door, and high touch surface 136 may be a side of the door. Here, TT layer 114 may be flexible or rigid. In examples where TT layer 114 is rigid, device 100 may be a rigid structure, e.g., planar, L-shaped, C-shaped or another rigid structure. In FIGS. 5 and 6, TT layer 114 is planar and may be flexible or rigid. In FIG. 7, TT layer 114 and thus device 100 may be L-shaped and extend about a corner 212 of structure 115. In this latter example, TT layer 114 and device 100 may be flexible or rigid.

In the illustrated example of FIG. 7, the device 100 may cover structure 115. Examples of using the device 100 for covering objects is further described with reference to FIGS. 24-39. In FIG. 7, the example device 100 may include an angled body 210 covering the corner 212 of the structure 115. The example light emitter 120 may include a flexible light emitter 220 coupled to interior 112 and facing exterior surface 116. Flexible light emitter 220 may include any now known or later developed light emitting element(s) capable of being flexed or bent into a desired position. In the illustrated example of FIG. 7, the flexible light emitter 2520 may include a flexible substrate 240 and one or more light emitting elements 242 therein or thereon. The example flexible substrate 240 may include, for example, a flexible printed circuit including the one or more light emitters 242 mounted thereon. Each light emitting element 242 may include one or more LED(s). Where desired, each light emitting element 242 may include one or more flexible LED(s). Flexible light emitter 220 may include an electroluminescent panel and/or light emitter 220 may include an organic light emitting diode (OLED) layer.

Figure 8:
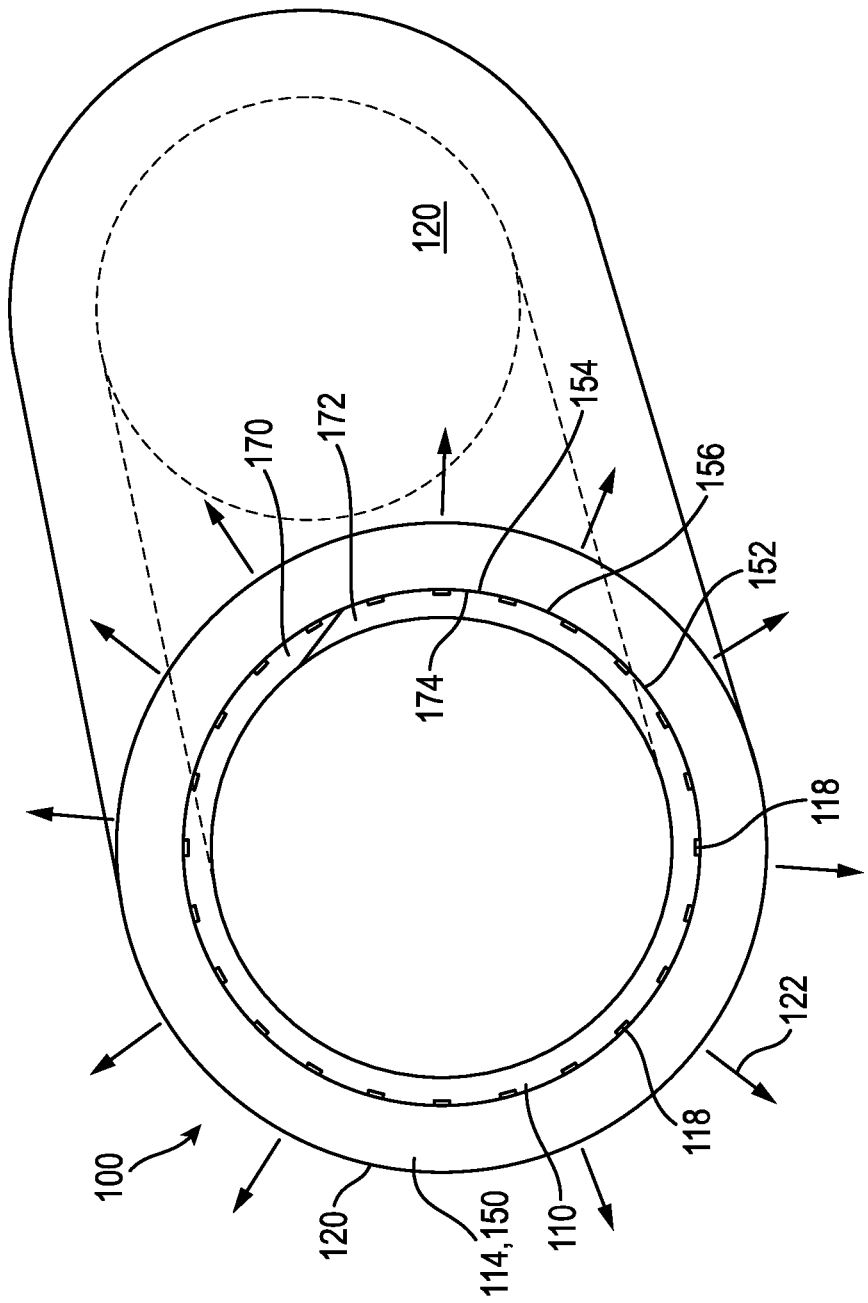
FIG. 8 shows a perspective view of a light emitting device and/or cover with a rigid transparent or translucent conduit according to systems, methods, and apparatuses of the present disclosure.
Figure 9:
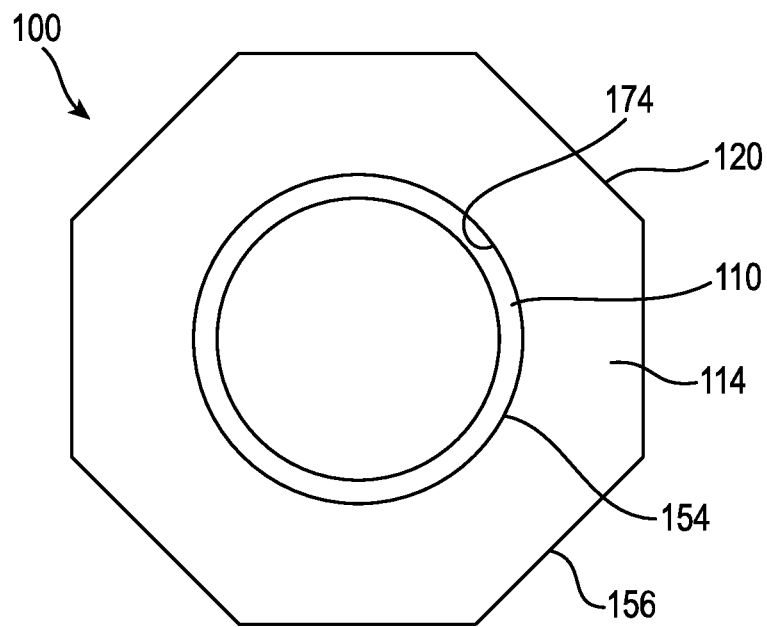
FIG. 9 shows a cross-sectional view of a light emitting device and/or cover with a rigid transparent or translucent conduit according to systems, methods, and apparatuses of the present disclosure.

In some examples, as shown in FIG. 8, TT layer 114 may be a conduit 150 having an elongated hollow interior 152. Here, flexible light emitting layer 110 may be positioned within conduit 150. TT layer 114 and thus conduit 150 may be rigid, e.g., of clear acrylic or diffuse polycarbonate plastic. In FIG. 8, interior surface 154 of rigid transparent or translucent tube 114 may have the same cross-sectional shape as exterior surface 120 of thereof. In some examples, the conduit 150 may have an exterior surface 120 and an interior surface 154 that are substantially cylindrical (e.g., conduit 150 is a tube). Other cross-sectional shapes may be possible. FIG. 9 shows a cross-section of another TT layer 114 that is a conduit, but may have an interior surface 154 of the conduit having a different cross-sectional shape than exterior surface 120 of the conduit. For example, the interior surface 154 may be cylindrical, having a circular cross-section, and the exterior surface 120 may have a hexagonal cross-section. Any exterior surface 120 configuration is possible. Flexible light emitting layer 110 may be coupled to interior surface 154 of rigid transparent or translucent conduit 150. Flexible light emitting layer 110 may be flush to interior surface 154 of rigid translucent or transparent conduit 150.

Returning to FIG. 1, some examples of device 100 may also include a control system 160. Control system 160 may be operatively coupled to flexible light emitting layer 110 and may be operative to control operational features of flexible light emitting layer 110 such as but not limited to: a duration of illumination, exiting light 122 color, light intensity, and/or light irradiance. Control system 160 may include any now known or later developed microcontroller. Device 100 may also include at least one sensor 162 coupled to control system 160 to provide feedback to control system 160. Sensor(s) 162 may sense any parameter of the control environment of device 100, including but not limited to: touch of device 100, heat of a user's hand on device 100, motion of a user, motion of structure 138 to which device 100 is coupled, temperature, light reception, and/or presence of microorganisms on exterior surface 120, etc. Sensor(s) 162 may include any now known or later developed sensing devices for the desired parameter(s). Control system 160 with (and without) sensor(s) may control operation to be continuous or intermittent based on external stimulus, and depending on the application. In one example, sensor(s) 162 may detect heat/human touch, motion, or light. Sensor(s) 162 may send the detected information to control system 160, which makes decisions on exiting light 122 being emitted through device 100, such as the color, intensity, or duration of disinfecting lighting. An example of this type of control may include a human touching a door (e.g., FIG. 6) that was previously illuminated with 405 nanometer light, once device 100 is touched, the sensor may detect that touch and may send information to control system 160, which may then make the decision to turn device 100 to disinfecting white light illumination while in use.

Device 100 may be powered through the use of batteries or rechargeable batteries mounted in proximity to the cover. Where rechargeable batteries are employed, they may be recharged, for example, using AC power or solar panels (not shown), where sufficient sunlight is available. Alternatively, device 100 may be provided with electrical connectors for hardwiring into AC power for applications where this is possible, such as in non-portable products like door handles or hand railings (e.g., FIGS. 5-6). Wireless or inductive charging may similarly charge or power device 100.

Figure 10:
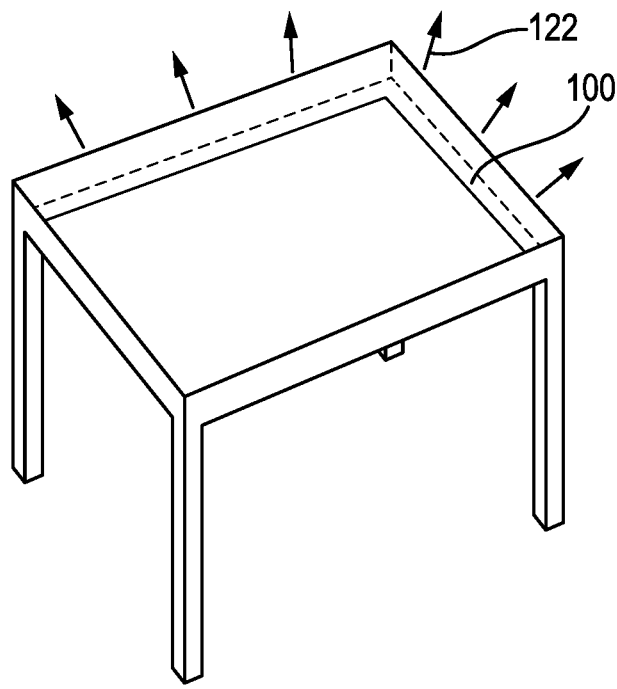
FIG. 10 shows a perspective view of a light emitting device and/or cover according to systems, methods, and apparatuses of the present disclosure on a table.
Figure 11:
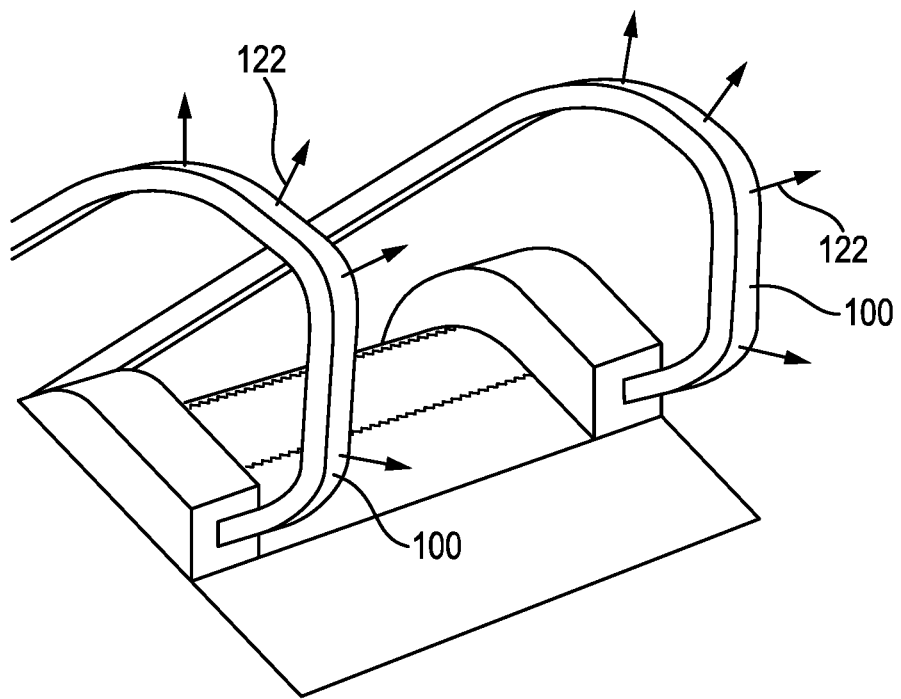
FIG. 11 shows a perspective view of a light emitting device and/or cover according to systems, methods, and apparatuses of the present disclosure on an escalator handle.
Figure 12:
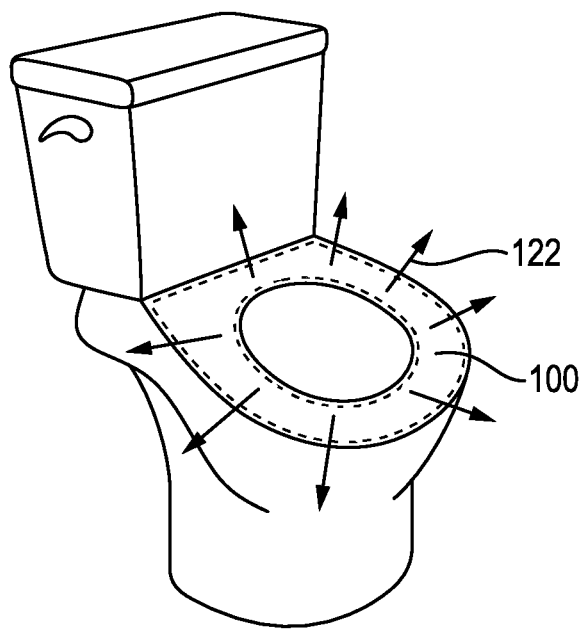
FIG. 12 shows a perspective view of a light emitting device and/or cover according to systems, methods, and apparatuses of the present disclosure on a toilet seat.
Figure 13:
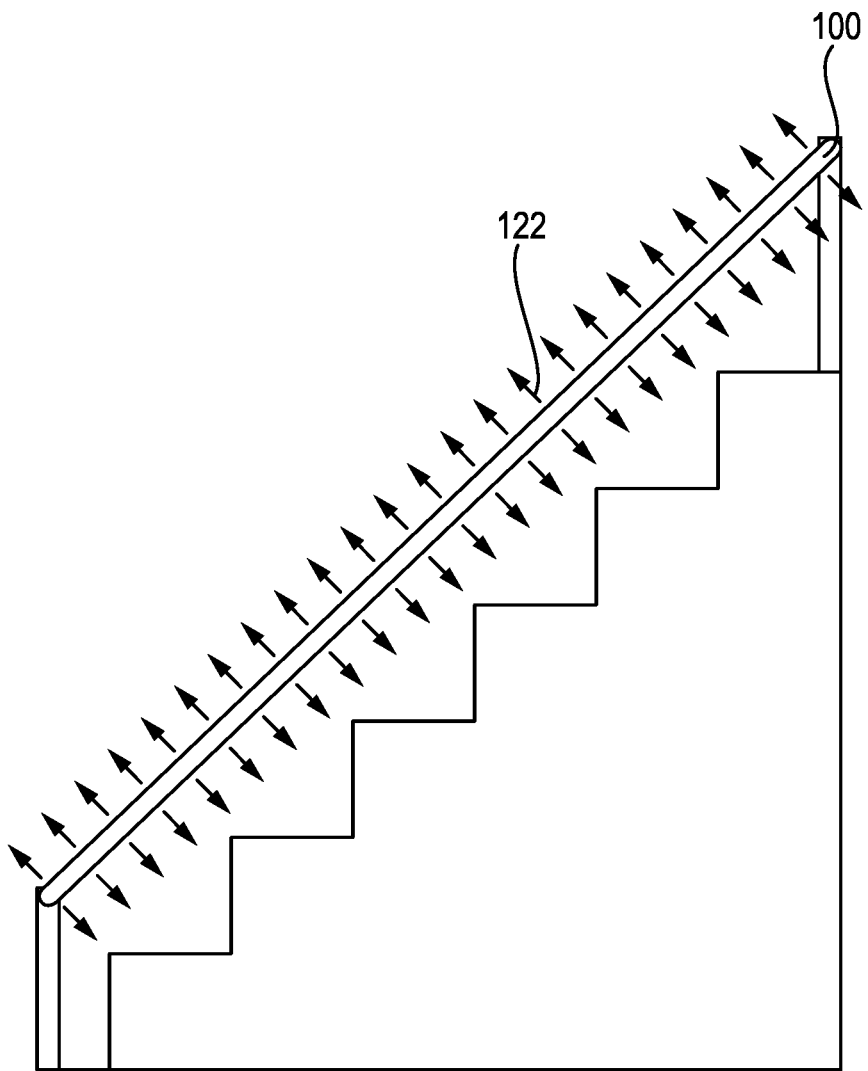
FIG. 13 shows a perspective view of a light emitting device and/or cover according to systems, methods, and apparatuses of the present disclosure on a stair handle.

FIGS. 10-13 show various non-limiting applications for device 100. FIG. 10 shows the device applied to a glass top table; FIG. 11 shows the device applied to a handrail of an escalator; FIG. 12 shows the device applied to a toilet seat; and FIG. 13 shows the device 100 applied to a stair handrail. A wide variety of other applications are possible.

Device 100 may provide a number of advantages. Device 100 may be configured to fit over practically any existing surface, which eliminates the need to redesign entire products in order to integrate the internally illuminated disinfecting technology into the product. Further, through the use of disinfecting wavelengths between 380-420 nm, e.g., 405 nm light, and prolonged exposure, device 100 has been found to effectively reduce the levels of microorganisms on a surface, such as bacteria, yeasts, and fungi. Since the germicidal wavelength range disclosed falls within visible light, unlike UV light, it is safe for continuous use around humans and animals, and the exterior surfaces being internally illuminated by these wavelengths may receive continuous disinfection, eliminating intermittent off periods where harmful microorganisms may grow and increase in volume. This ability is beneficial since high touch surfaces are typically constantly contacted by multiple humans and need to be disinfected continuously to create a safe environment. Because device 100 may conform to any shape, it may be applied to practically any surface, such as hand railings and door handles. For example, any planar high touch surface, either of flat or unequal elevation, may be retrofitted with an internally illuminated disinfecting surface device 100. Device 100 may also be applied anywhere, even where shadows would normally prevent disinfecting light from reaching a surface. The light wavelengths described herein also do not degrade materials, e.g., plastics, with which it comes into contact.

Referring to FIGS. 14-21, and again FIGS. 8 and 9, a method for producing a light emitting device 100 is illustrated. Conduit 150 may be tubular, as in FIG. 8, or may have other exterior surface cross-sections, as in FIG. 9. Interior surface 154 of conduit 150 is shown as cylindrical, but it may vary from cylindrical depending on the degree of flexibility of flexible light emitting layer 110 and its ability to comport with interior surface 154.

Figure 14:
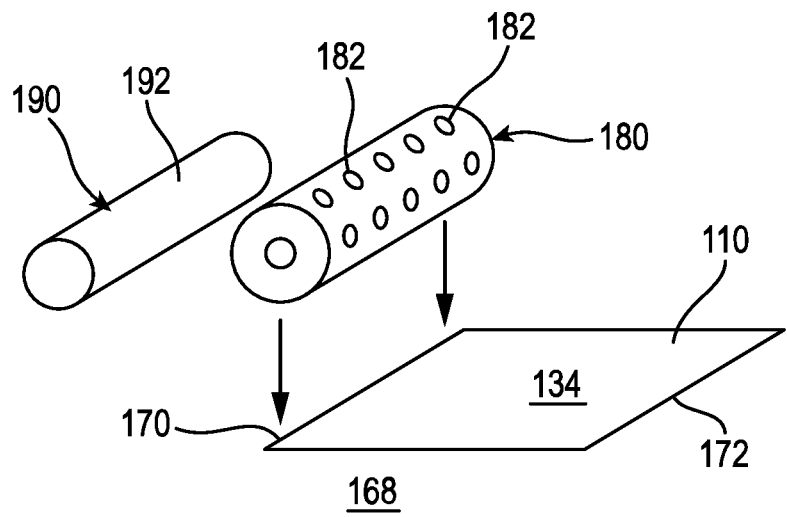
FIG. 14 shows a perspective view of a step of a method of producing light emitting device and/or cover with a rigid transparent or translucent conduit according to systems, methods, and apparatuses of the present disclosure.
Figure 15:
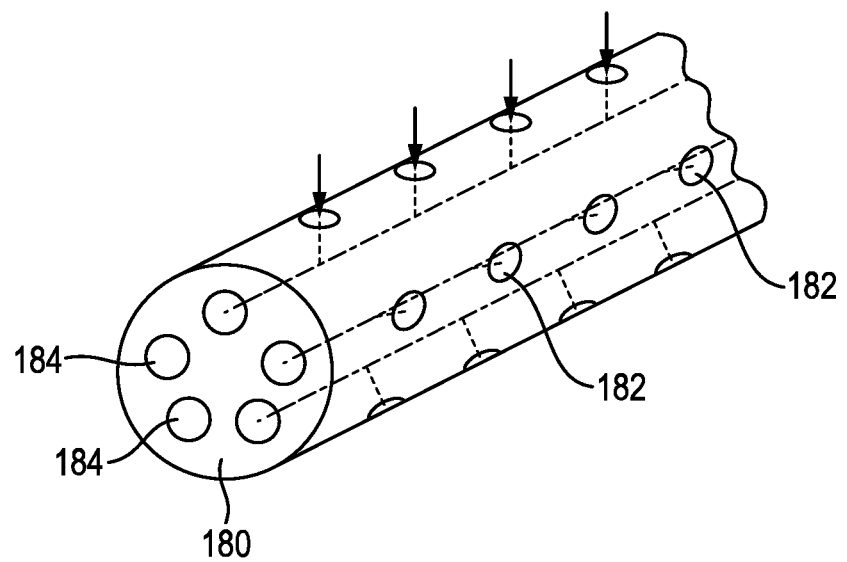
FIG. 15 shows a perspective view of a mandrel for use with a step of a method of producing light emitting device and/or cover with a rigid transparent or translucent conduit according to systems, methods, and apparatuses of the present disclosure.

As shown in FIG. 14, the method may include supporting flexible light emitting layer 110, e.g., on a surface. The supporting may be on any now known or later developed planar support 168, e.g., a table top, manufacturing platen, etc. Flexible light emitting layer 110 may have a first end 170 and a second end 172, and an exterior surface 174 (bottom surface as shown, with back surface 134 up). A cylindrical mandrel 180 or 190 may be provided upon which flexible light emitting layer 110 will be rolled. In some examples, cylindrical mandrel 180 may include openings 182 in a surface thereof for applying pressure to flexible light emitting layer 110, e.g., inward vacuum or outward pressure. As shown in FIG. 15, cylindrical mandrel 180 may include any necessary internal channels and/or pressure lines 184, pumps/vacuums and control systems to control the pressure applied via openings 182. Cylindrical mandrel 190 may include a surface 192 upon which an adhesive may be applied for adhering to flexible light emitting element 110.

Figure 16:
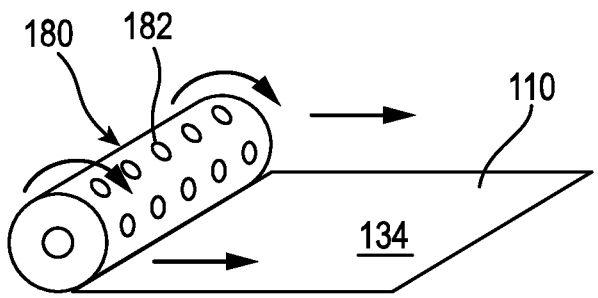
FIGS. 16-19 show perspective views of steps of a method of producing light emitting device and/or cover with a rigid transparent or translucent conduit according to systems, methods, and apparatuses of the present disclosure.
Figure 17:
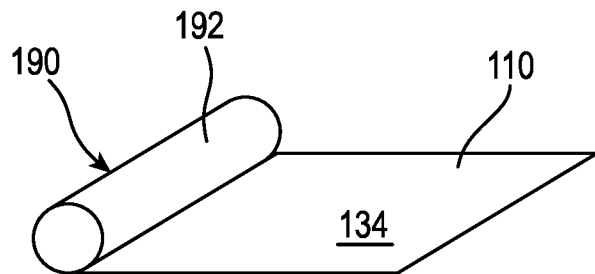

FIGS. 16 and 17 show linearly advancing and rotating cylindrical mandrel 180 or 190, respectively, in contact with flexible light emitting layer 110 while adhering at least a portion of cylindrical mandrel 180 or 190 to flexible light emitting layer 110 to cause flexible light emitting layer 110 to roll onto cylindrical mandrel 180 or 190. In FIG. 16, the adhering may include applying a vacuum across at least a portion of cylindrical mandrel 180, via openings 182, to cause flexible light emitting layer 110 to roll onto cylindrical mandrel 180. In FIG. 17, the adhering may include using adhesive or sealant on at least a portion of surface 192 of cylindrical mandrel 190 to cause the flexible light emitting layer to roll onto cylindrical mandrel 190. Where adhesive is employed, it may be temporary. In this case, the temporary adhesive for attaching flexible light emitting layer 110 to cylindrical mandrel 180 may last only as long as flexible light emitting layer 110 is required to be adhered to the mandrel from the time flexible light emitting layer 110 is picked up by the mandrel to when it is in its final resting place within conduit 150. At that time, the temporary adhesive may un-adhere, wear off, or otherwise release, to allow the mandrel to be retracted from the conduit, if the mandrel is not maintained within conduit as a heat sink or support. The temporary adhesive may be treated in some fashion to cause it to un-adhere, wear off, or otherwise release, e.g., with heat. Other mechanism to cause flexible light emitting layer 110 to adhere to cylindrical mandrel 180 may also be possible, e.g., electrostatics, magnetism, etc. Once rolled onto cylindrical mandrel 190, flexible light emitting layer 110 has a conduit form.

Figure 18:
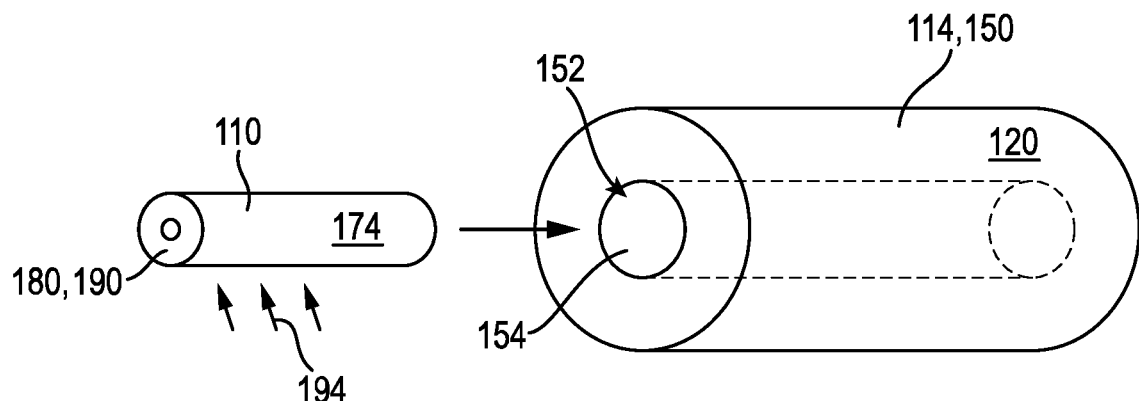

As an alternative at this stage, and as shown in FIG. 18, at least one of an adhesive and a sealant 194 may be applied to exterior surface 174 of flexible light emitting layer 110, e.g., prior to placing flexible light emitting layer 110 in conduit form into rigid transparent or translucent conduit 150.

Figure 19:
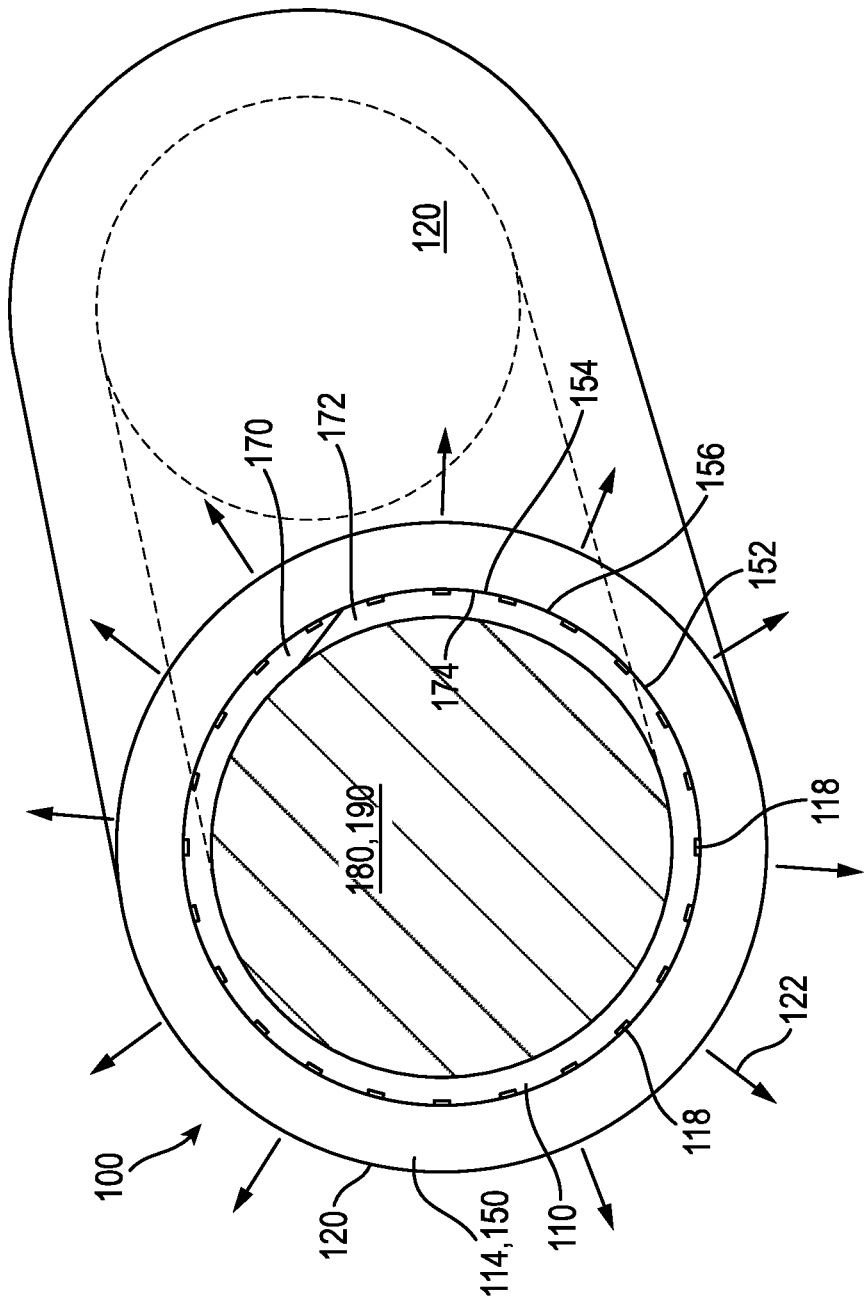

FIG. 18 also shows placing flexible light emitting layer 110 in the conduit form into a rigid transparent or translucent conduit 150 (in the direction of the arrow) to form light emitting device 100 (FIGS. 8, 9 and 19). The placing may include inserting mandrel 180, 190 with flexible light emitting layer 110 thereon into elongated hollow interior 152 of transparent or translucent conduit 150. Interior surface 154 may have a size, e.g., diameter or cross-sectional area, configured to receive mandrel 180 or 190 with flexible light emitting layer 110 thereon.

Figure 20:
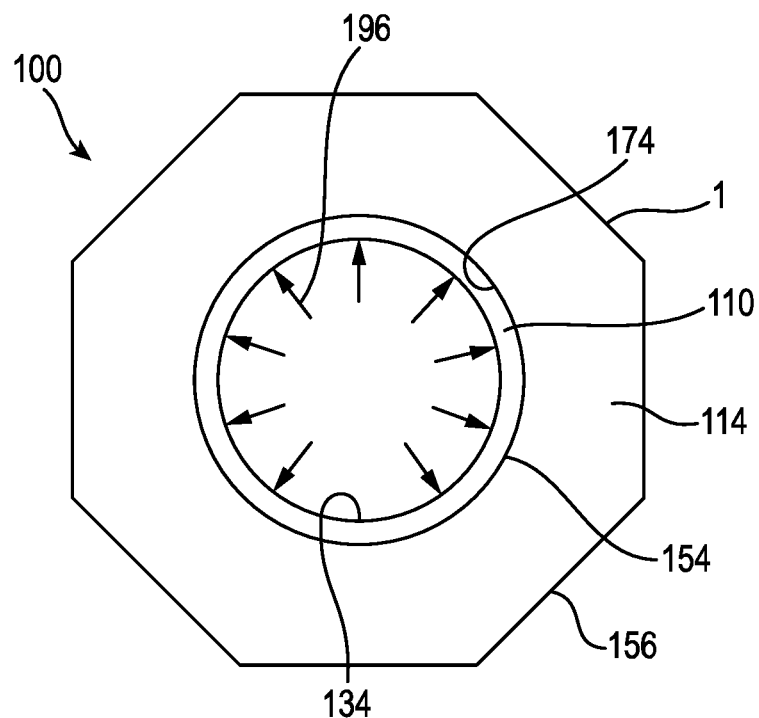
FIG. 20 shows a cross-sectional view of a step of a method of producing light emitting device and/or cover with a rigid transparent or translucent conduit according to systems, methods, and apparatuses of the present disclosure.
Figure 21:
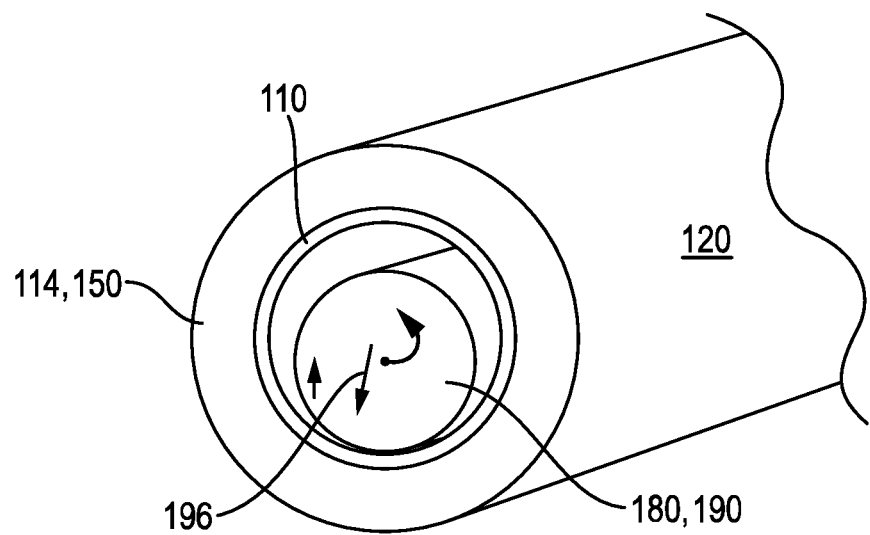
FIG. 21 shows a perspective view of a step of a method of producing light emitting device and/or cover with a rigid transparent or translucent conduit according to systems, methods, and apparatuses of the present disclosure.

As shown in FIGS. 19 and 20, coupling exterior surface 174 of flexible light emitting layer 110 to interior surface 154 of rigid transparent or translucent conduit 150 may be performed next. As shown in FIG. 19, where the adhering includes applying a vacuum across at least a portion of cylindrical mandrel 180 to cause flexible light emitting layer 110 to roll onto the cylindrical mandrel (as in FIG. 16), the coupling may include releasing the vacuum and allowing flexible light emitting layer 110 to expand into and comport to interior surface 154 of rigid transparent or translucent conduit 150. This process relies on the flexibility of flexible light emitting layer 110 to be sufficiently strong to force the layer 110 to comport to interior surface 154. When unfurled, flexible light emitting layer 110 will allow light 112 to travel into rigid transparent or translucent conduit 150, regardless of the latter's exterior surface shape. A length of flexible light emitting layer 110 may be configured to ensure none of, or only desired portions of, interior surface 154 of conduit 150 is not covered by layer 110. In the illustrated example of FIG. 19, first and second ends 170, 172 may be angled to overlap and slidably engage to ensure layer 110 sufficiently covers the interior surface 154 of conduit 150. Alternatively, as shown in the example of FIGS. 20 and 21, the coupling may further include applying a pressure 196 across at least a portion of an interior surface (back surface 134) of flexible light emitting layer 110 using cylindrical mandrel 180 or 190 to force exterior surface 174 of flexible light emitting layer 110 to comport with interior surface 154 of rigid transparent or translucent conduit 150. As shown in FIG. 20, pressure 196 may be applied via openings 182 in mandrel 180.

Alternatively, as shown in FIG. 21, pressure 196 may be applied by moving mandrel 180 or 190 within flexible light emitting layer 110. Pressure 196, as applied in FIG. 21, may also act to un-adhere flexible light emitting layer 110 from mandrel 190, where adhesive (FIGS. 14, 17) is employed.

In some examples, cylindrical mandrel 180, 190 may be removed, leaving an interior of flexible light emitting layer 110 in the conduit form empty. This may, for example, allow air to cool layer 110. Alternatively, as shown in FIG. 19, cylindrical mandrel 180, 190 may be left in flexible light emitting layer 110. In this case, mandrel 180, 190 may provide support and/or act as a heat sink. While particular sequences of steps have been shown relative to the figures, it is understood that various steps may be switched between examples and the sequences altered between examples.

Figure 22:
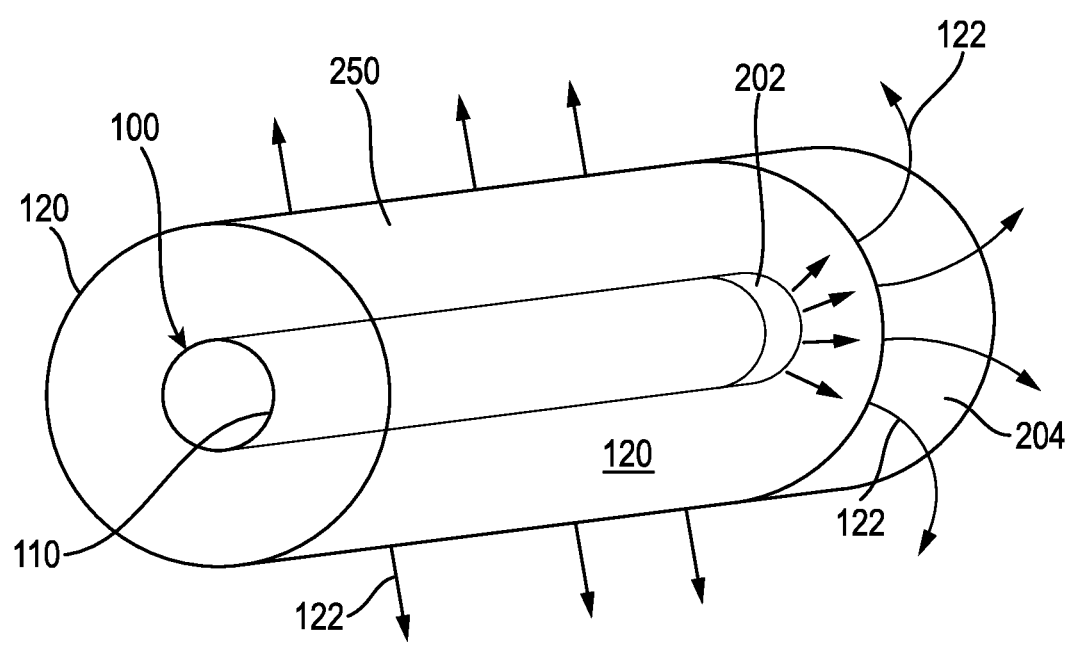
FIG. 22 shows a perspective view of another application of a light emitting device and/or cover according to systems, methods, and apparatuses of the present disclosure.

Referring to FIG. 22, a perspective view of another application of light emitting device 100 is illustrated. In the illustrated example, light emitting device 100 may be coupled to a transparent or translucent member 200 such as a (rigid) hand rail. Here, light emitting device 100 may also include a terminal light emitter 202 to transmit exiting light 122 out a terminal end 204 of transparent or translucent member 200. Terminal end 204 may be any structure that terminates or ends member 202, e.g., a terminus or capped end of a hand rail or handle. Terminal end 204 may take any shape, e.g., cylindrical, bulbous, etc., and may be transparent or translucent similar to member 202. Terminal light emitter 202 may take any light emitter form capable of emitting light out terminal end 204, e.g., LEDs, LEDs with light-converting layer(s), laser, etc., and may be shaped to fit within member 202 or at an end thereof such that light may emit out through terminal end 204. Terminal light emitter 202 may emit exiting light 122 that is identical to that described herein. Thus, terminal end 204 may have the same color as the member 202, and/or may have its exterior surface disinfected where such light is created by terminal light emitter 202.

Figure 23A:
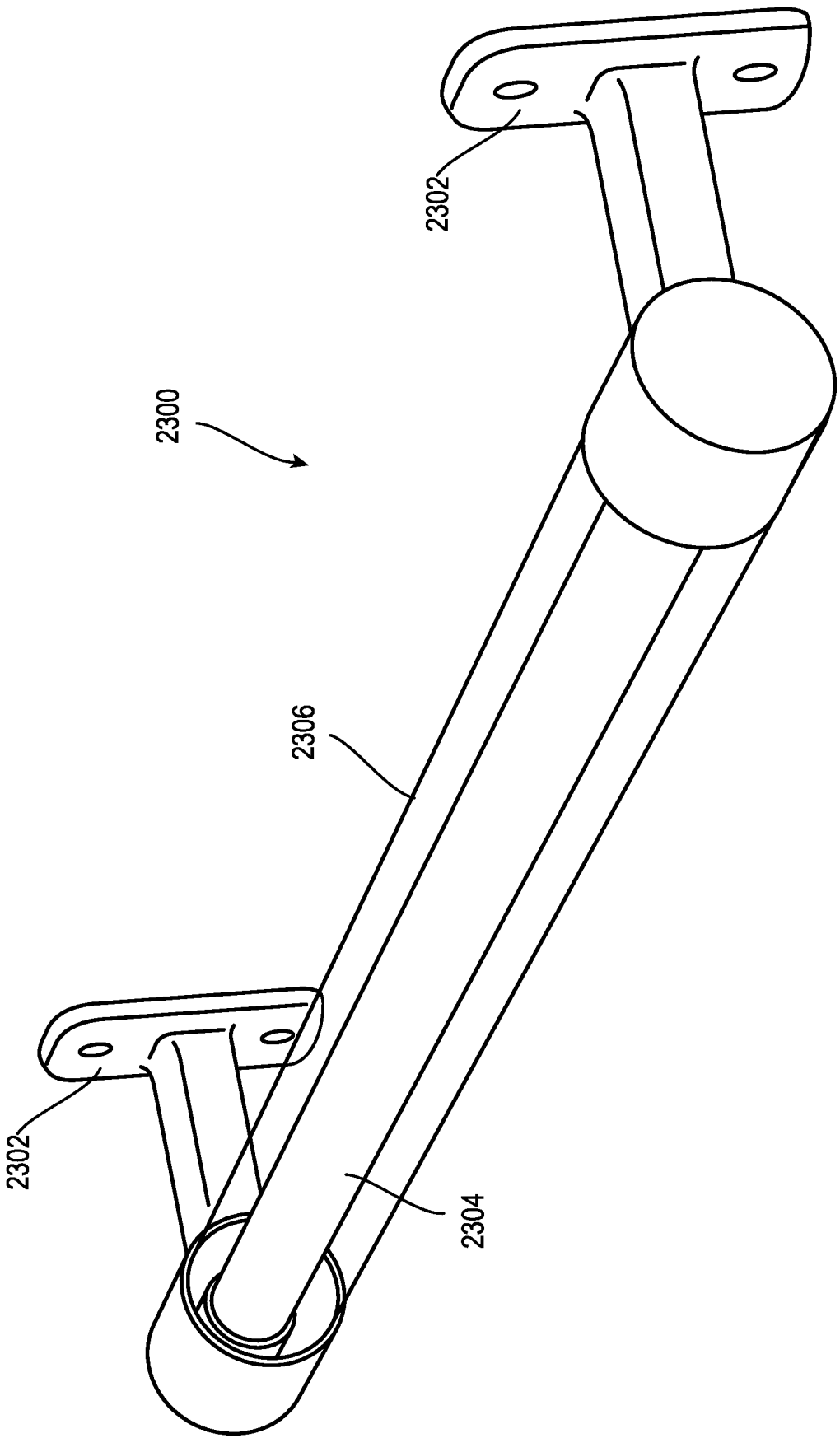
FIGS. 23A-23B show perspective views of a device and/or cover according to systems, methods, and apparatuses of the present disclosure.
Figure 23B:
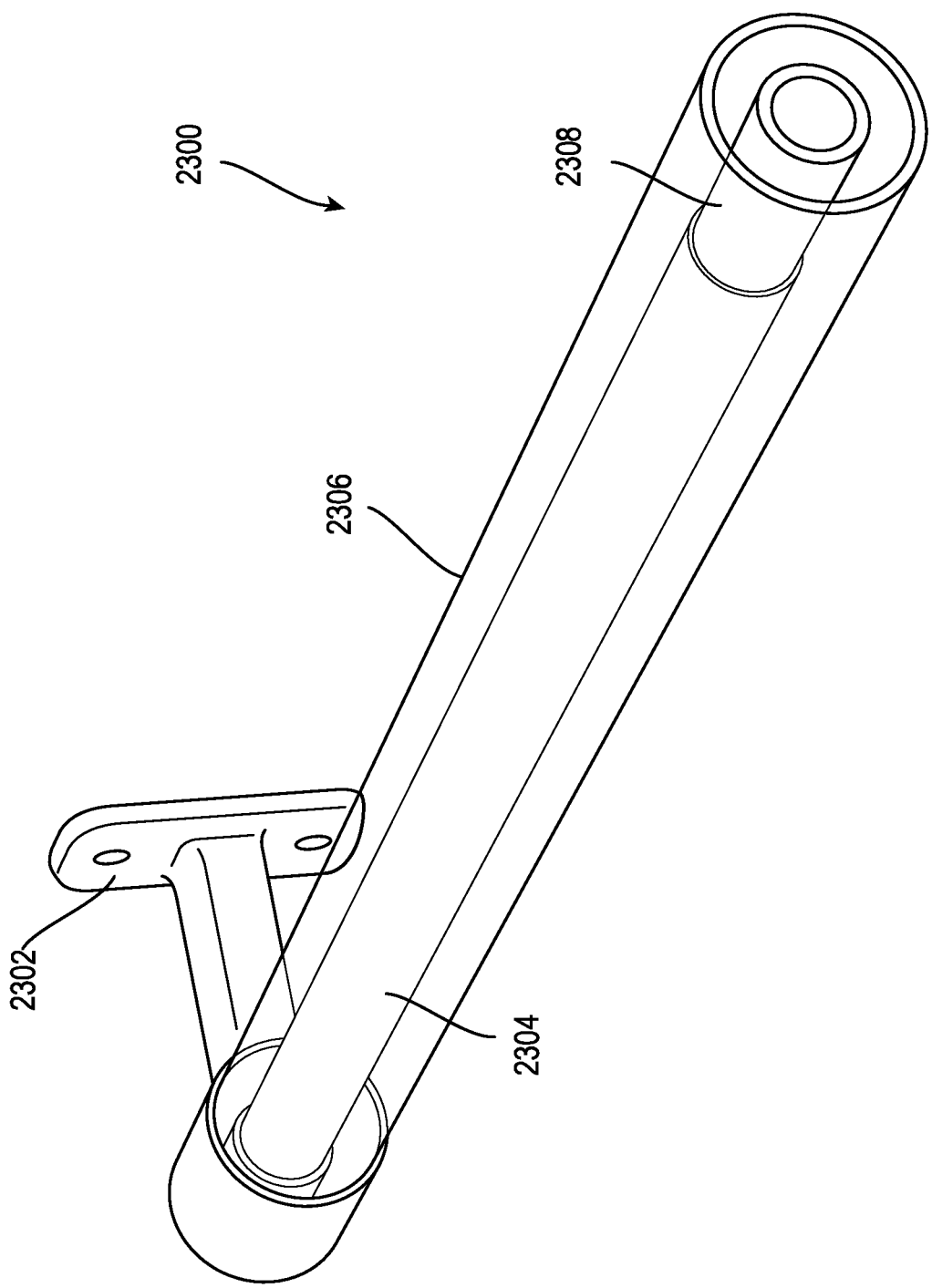

FIGS. 23A-23B illustrate an example light emitting device 2300. The example light emitting device 2300 may be attached to a structure (not shown) via one or more endcaps 2302. The example light emitting device 2300 may comprise a flexible light emitting layer 2304, a translucent tubular layer 2306, and an internal cylinder 2308 (e.g., a mandrel) (FIG. 23B). The example flexible light emitting layer 2304 may not be flush with the translucent (or transparent) tubular layer 2305.

As shown in FIG. 23B, the example flexible light emitting layer 2304 may be wrapped around the internal cylinder 2308. The flexible light emitting layer 2304 may be adhered or mechanically fastened to the internal cylinder 2308. In some examples, the internal cylinder 2308 may act as a heat sink. For example, the internal cylinder 2308 may comprise a heat conductive material such as, for example, metal (e.g., aluminum) and/or plastic. In some examples, the translucent tubular layer 2306 may not contact the internal cylinder 2308. In some examples, the internal cylinder 2308 may have a smaller diameter than the translucent tubular layer 2306, such that the flexible light emitting layer 2304 may be offset from the translucent tubular layer 2306 (e.g., by 0.01 or 0.02 inches). In some examples, the flexible light emitting layer 2304 may be wrapped around the internal cylinder 2308, and the translucent tubular layer 2306 may be flush against the flexible light emitting layer 2304.

In some examples, the flexible light emitting layer 2304 may comprise a flexible printed circuit board comprising one or more disinfecting LEDs. In some examples, the internal cylinder 2308 may be held in place by the one or more endcaps 2302. The internal cylinder 2308 may be solid, a hollow tube, or rectangular, square, ellipses, or circular in cross-section. The internal cylinder 2308 may have a different cross-section (e.g., shape, size, etc.) than the translucent tubular layer 2306.

Figure 24:
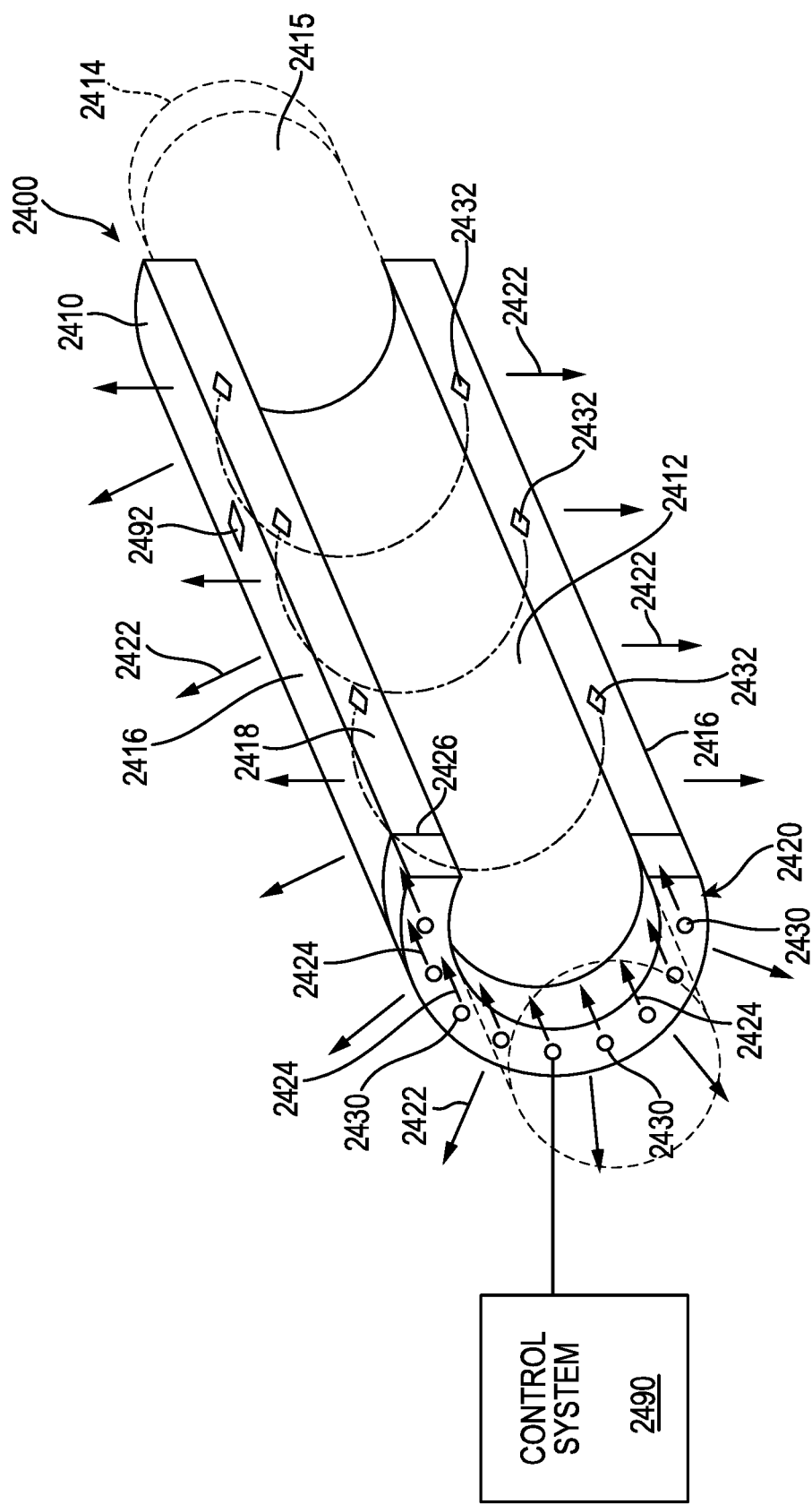
FIGS. 24-25 show perspective views of a device and/or cover according to systems, methods, and apparatuses of the present disclosure.

In some examples, a light emitting cover may inactivate microorganisms and may be configured to cover at least a portion of a high touch surface. FIG. 24 shows a perspective view of an example light emitting cover 2400 (hereinafter "cover 2400"). Cover 2400 may include a body 2410 having an interior 2412 configured to cover at least a portion of a high touch surface 2414 of an associated structure 2415. Interior 2412 may include a surface and/or other structure necessary to mate with or otherwise conceal high touch surface 2414. Structure 2415 includes high touch surface 2414 and may be practically any object, surface, or thing. One example structure 2415 for which cover 2400 is beneficial is any sort of handle grasped by users, e.g., a door handle, refrigerator handle, etc.

Body 2410 may also include an exterior surface 2416 configured to be disinfected. Exterior surface 2416 replaces high touch surface 2414 as the outside part or layer of structure 2415 to which cover 2400 is coupled. At least an exterior portion 2418 of body 2410 may be transparent or translucent. That is, at least an exterior portion 2418 of body 2410, immediately within or near exterior surface 2416, may be transparent or translucent such that light may travel therethrough and exit exterior surface 4216. As used herein, "transparent" or "translucent" indicate any level of light transmission short of opaque. A portion of body 2410 (not shown) through which light 2424 transmission may not necessarily be transparent or translucent. Body 2410 may be made of any material capable of having exterior portion 2418 transparent or translucent, e.g., clear polymer, rubber, glass, etc.

Cover 2400 also includes a light emitter 2420 operably coupled to body 2410 for emitting a light 2422 (arrows) (hereinafter "exiting light 2422") through exterior surface 2416. Exiting light 2422 exiting exterior surface 2416 may have at least a portion thereof having a wavelength in a range of approximately 380 to approximately 420 nanometers (nm). This wavelength of light may kill microorganisms on surfaces. Exiting light 2422 may have at least a portion thereof at a wavelength of 405 nm. Exiting light 2422 may be solely of 380 to 420 nm, exiting light 2422 may be converted to different wavelengths, and/or exiting light 2422 may be combined with different light emitters with different wavelengths and/or with variable wavelengths, to create disinfecting light of another color such as white light. Exiting light 2422 may have any irradiance or intensity sufficient to disinfect exterior surface 2416 that may be touched, which may vary depending on, for example: the type of material of body 2410, the level of microorganisms thereon, the extent of touching (e.g., low level bedroom door handle versus high level grocery cart handle), the type of application, etc. Exiting light 2422 may have an irradiance of no less than 0.01 mW/cm$^2$, e.g., from all or at least part of exterior surface 2416.

Light emitter 2420 may take a variety of forms. In illustrated example of FIG. 24, light emitter 2420 may be operative to direct light 2424 (prior to exiting light 2422 exiting exterior surface 2416) into body 2410 and out exterior surface 2416. In FIG. 24, light emitter 2420 emits light through an edge 2426 of body 2410 between interior 2412 and exterior surfaces 2416. Edge lighting may be beneficial because fewer light emitters, such as LEDs, may be needed. Edge lighting may also be considered more aesthetically pleasing because individual light source points cannot be seen along cover 2400, instead a uniform light is seen. Light emitter 2420 may include any form of light emission element capable of creating the desired wavelength of light an introducing it to body 2410. Light emitter 2420 may include one or more light emitting diodes (LEDs) 2430. LEDs 2430 may be coupled to edge 2426 via a separate structure or fixedly coupled to edge 2426. Alternatively, LEDs 2430 may be embedded within body 2426. As shown in FIG. 24, cover 2410 may include a waveguide(s) 2432 within body 2410 for directing the light 2424 to exterior surface 2416, and out as exiting light 2422. Waveguide(s) 2432 may include any now known or later developed optical device for directing, confining or conveying light waves. For example, instead of electroluminescent wire, waveguide(s) 2432 may include fiber optic diffuser elements bonded within exterior surface 2416, and illuminated by lasers to provide illumination to through exterior surface. Light 2424 and/or exiting light 2422 may have any color desired, so long as sufficient light to disinfect in the 380-420 nm range is present therein.

Figure 25:
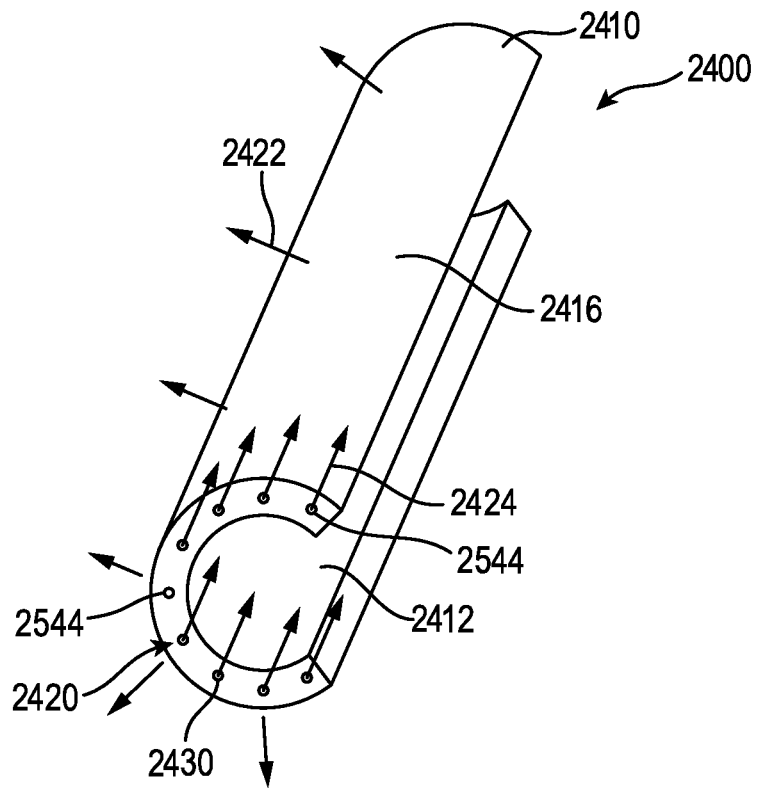
Figure 26:
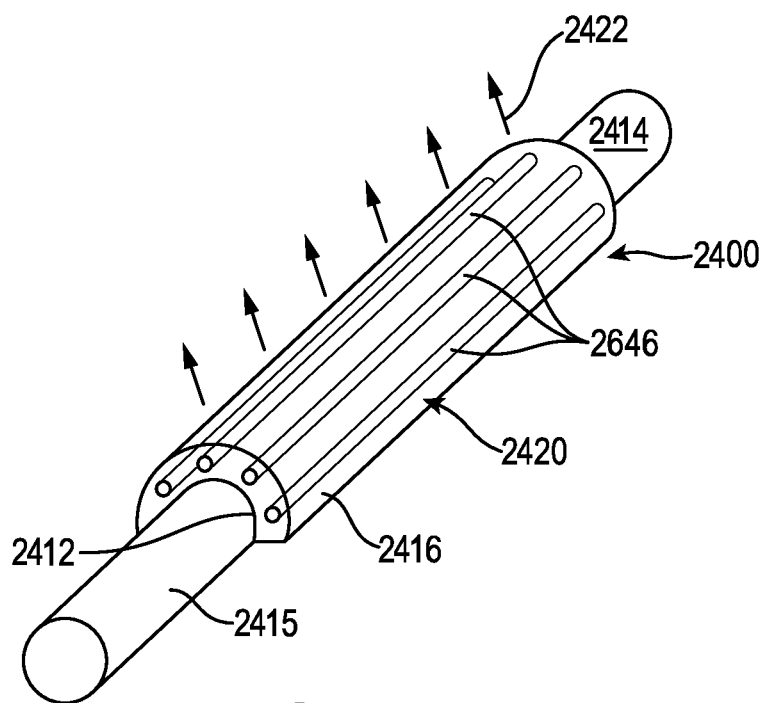
FIG. 26 shows a perspective view of a device and/or cover on a high touch surface according to systems, methods, and apparatuses of the present disclosure.

Referring to FIGS. 25 and 26, light emitter 2420 may be embedded within body 2410 between interior 2412 and exterior surface 2416. In FIG. 25, light emitter 2420 may include LEDs 2544 embedded near an end of body 2410, and in FIG. 26, light emitter 2420 may include electroluminescent wire(s) 2646 that extend at least a portion of body 2410. Light emitter 2420 may include any number of actual emitters necessary to disinfect exterior surface 2416 and create the desired color, intensity, irradiance, etc.

Light emitter 2420 may emit light 2424 that may be the same as that which exits exterior surface 2416. In one example, exiting light 2422 may include exclusively light having the wavelength in the range of 380 to 420 nanometers. Alternatively, light emitter 2420 may be controlled to emit a variety of other different wavelengths and colors, but including some portion that is in the range of 380 to 420 nanometers sufficient to disinfect exterior surface 2416. Any color or intensity may be achieved in this manner, e.g., to match a color of structure 2415. Alternatively, light 2424 may be converted at some point during its travel prior to exiting exterior surface 2416 as exiting light 2422. For example, light 2424 may be converted to a white light having a portion thereof with the wavelength in the range of 380 to 420 nanometers, but also other wavelengths of light, e.g., 450-500 nm and 550-700 nm, to create the white light. For example, 450-500 nm light may be produced using blue phosphors and 550-700 nm light may be produced using nitride phosphors. Other colors of light may also be generated in this manner.

Figure 27:
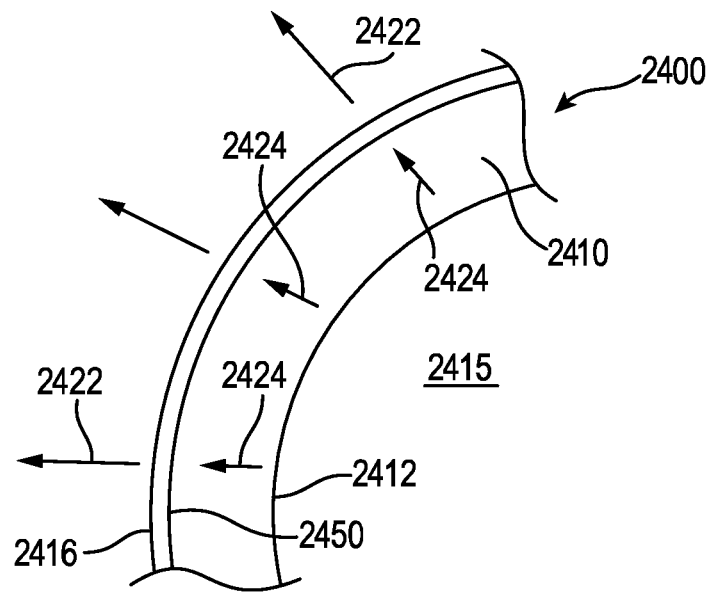
FIG. 27 shows a partial cross-sectional view of a device and/or cover including a light-converting layer according to systems, methods, and apparatuses of the present disclosure.

In the illustrated example of FIG. 27, body 2410 may include a light-converting layer 2450 through which light 2424 travels to convert a portion of the light to a wavelength(s) different from the wavelength of the light 2424 emitted from light emitter 2420. In FIG. 27, light-converting layer 2450 is embedded in body 2410 near exterior surface 2416; however, it may be located anywhere along a path of light 2424. Light-converting layer 2450 may include any now known or later developed layer(s) for converting all or certain portion(s) of light 2424 to different wavelengths. Light-converting layer 2450 may include at least one phosphor, at least one optical brightener and/or at least one quantum dot. Light-converting layer 2450 may tune light 2422 to, for example, alter a color tint of exterior surface 2416 or the color tint of the material directly surrounding each of light emitters 2430, 2646, etc., internal to cover 2400. Light-converting layer 2450 may be segmented across the layer's surface to convert light 2424 to two or more different wavelengths, e.g., one segment to allow some of light 2424 to pass unconverted, another segment to convert some of light 2424 to another wavelength, and another segment to convert some of light 2424 to yet another wavelength. In any event, light 2422 may be customized to provide disinfection and a desired color. In one non-limiting example, light 2422 may have a color rendering index (CRI) value of at least 70, a correlated color temperature (CCT) between approximately 2,500 K and 5,000 K and/or a proportion of spectral energy measured in the 380 nm to 420 nm wavelength range between 10% and 44%.

Figure 28:
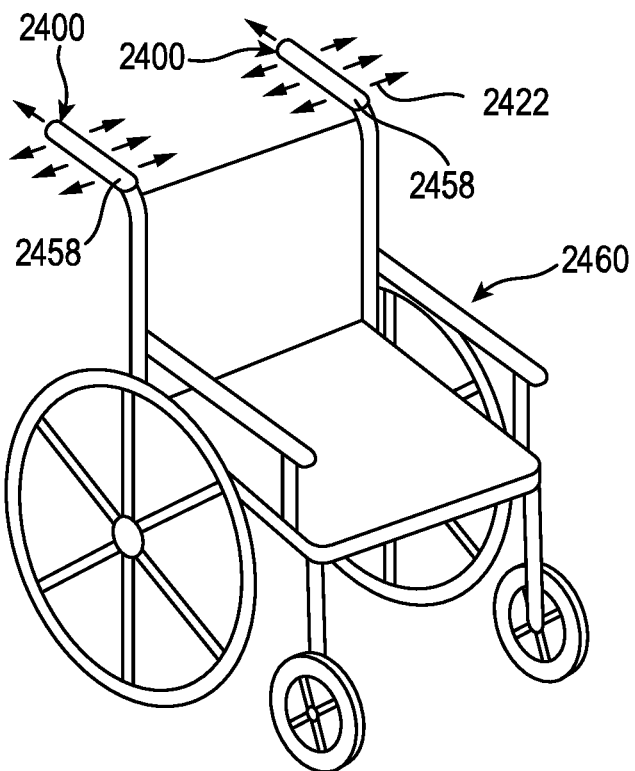
FIG. 28 shows a perspective view of a device and/or cover according to systems, methods, and apparatuses of the present disclosure on a wheel chair handle.
Figure 29:
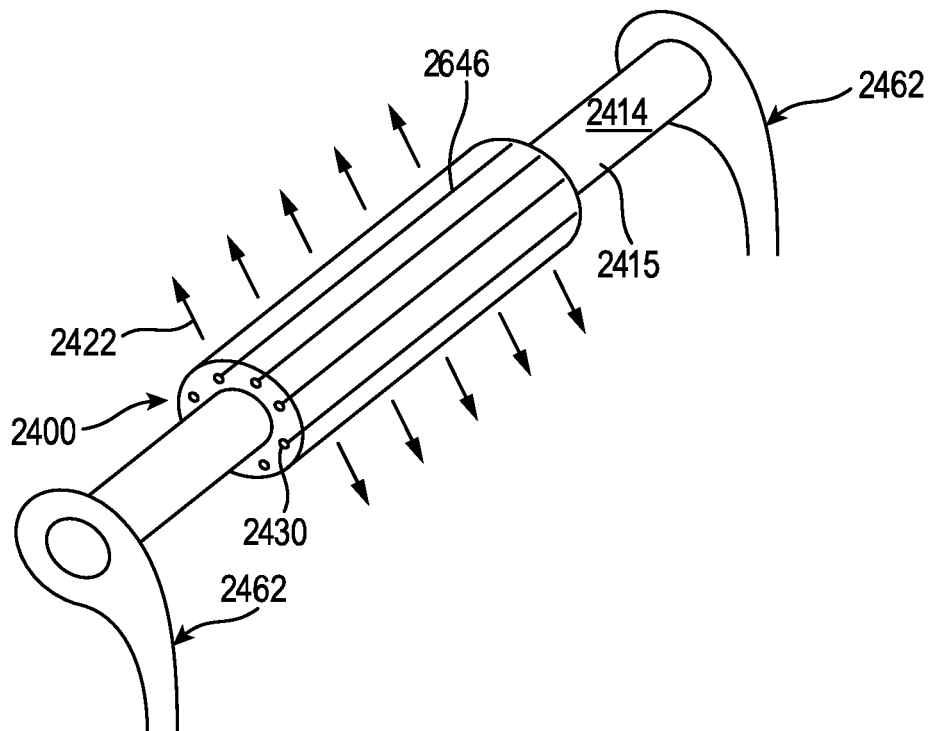
FIG. 29 shows an enlarged perspective view of a device and/or cover according to systems, methods, and apparatuses of the present disclosure on a grocery cart.
Figure 30:
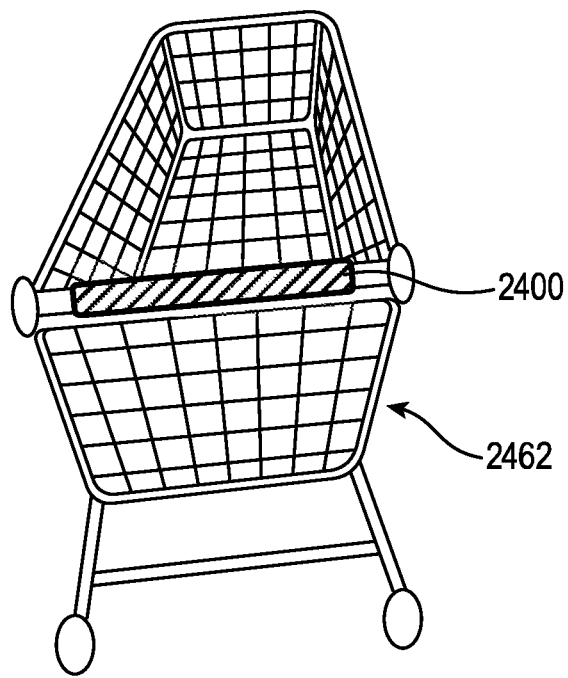
FIG. 30 shows a perspective view of a device and/or cover according to systems, methods, and apparatuses of the present disclosure on a grocery cart.
Figure 31:
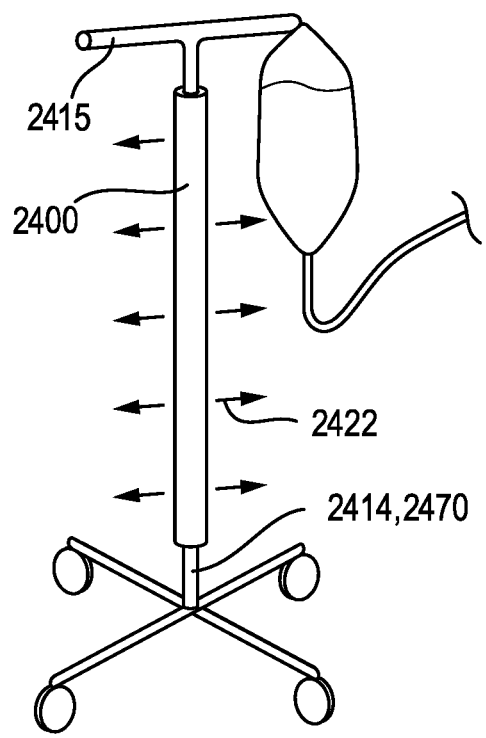
FIG. 31 shows a perspective view of a device and/or cover according to systems, methods, and apparatuses of the present disclosure on an IV bag stand.
Figure 32:
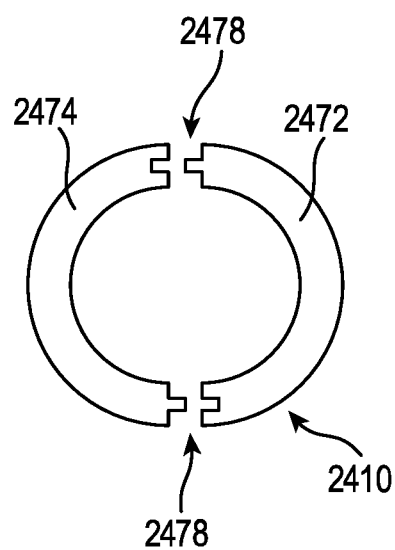
FIG. 32 shows a cross-sectional view of a segmented device and/or cover according to systems, methods, and apparatuses of the present disclosure.
Figure 33:
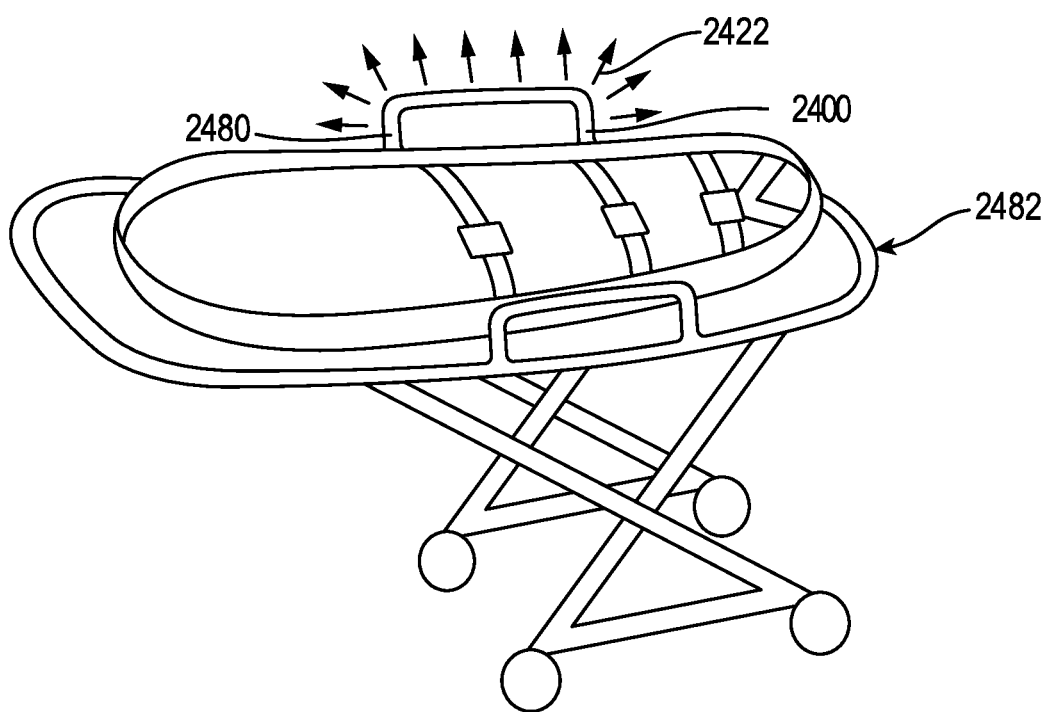
FIG. 33 shows a perspective view of a device and/or cover according to systems, methods, and apparatuses of the present disclosure on a hospital bed.
Figure 34:
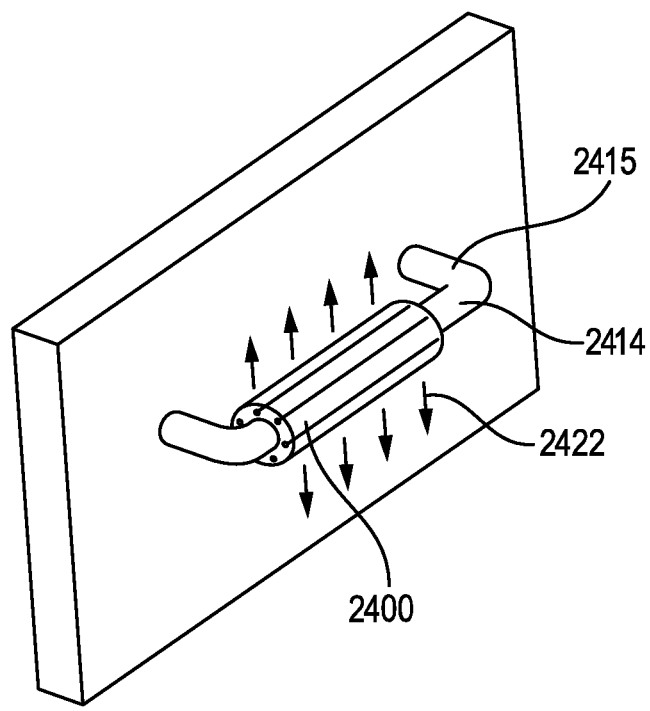
FIG. 34 shows a perspective view of a device and/or cover according to systems, methods, and apparatuses of the present disclosure on a drawer handle.
Figure 35:
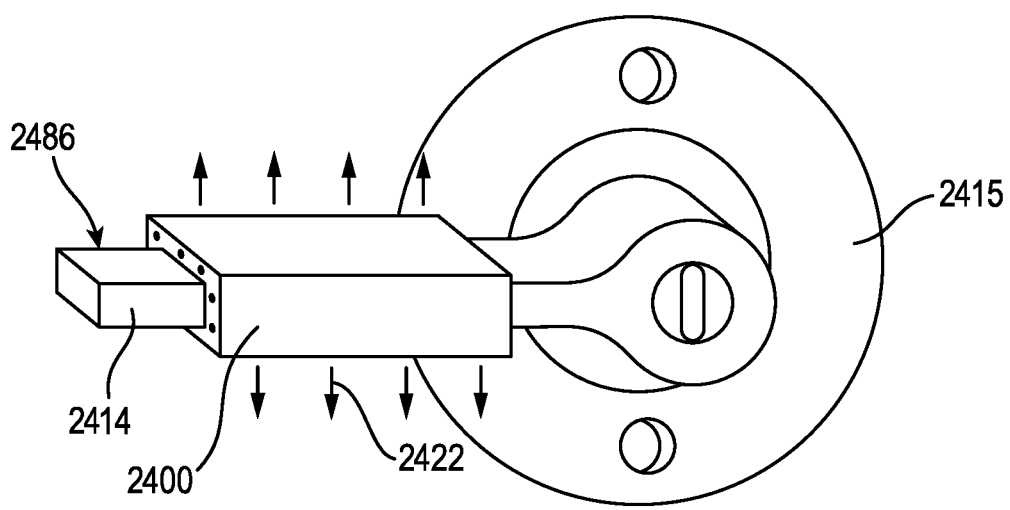
FIG. 35 shows a perspective view of a device and/or cover according to systems, methods, and apparatuses of the present disclosure on a door handle.

With further regard to body 2410, the body may take any form necessary to allow it to cover the desired portions or all of a respective high touch surface 2414. In the illustrated example of FIGS. 24-26, cover 2400 may comprise a "C"-shape, e.g., to cover a rounded or partially rounded high touch surface 2414. In some examples, body 2410 may be flexible to allow a snap-fit of interior 2412 onto high touch surface 2414. In this form, body 2410 may be readily mounted to a round high touch surface 2414 such as those on a handle 2458 of a wheelchair 2460, as shown in FIG. 28, or a grocery cart handle 2462, as shown in FIGS. 29 and 30. Here, interior 2412 may be shaped to mate with high touch surface 2414, e.g., match an exterior surface of structure 2415. In addition to the snap fit or in replacement thereof, fasteners (such as mechanical fasteners 168 shown and described with reference to FIG. 7) or adhesives may be employed through or over body 2410. In the illustrated example of FIG. 31, body 2410 may be tubular and is shaped to mate with high touch surface 2414, e.g., matches a cylindrical surface. In some examples, the body 2410 may merely be wrapped around a surface. In FIG. 31, structure 2415 may include a cylindrical support pole 2470 of an intravenous (IV) bag stand. Body 2410 may be a unitary piece that slides over structure 2415. In the illustrated example of FIG. 32, body 2410 may include at least two arcuate members 2472, 2474 configured to be coupled to form a circular cross-section body. Any number of arcuate members may be employed and they may be coupled using any now known or later developed fastener 2478, e.g., male/female latches, hook-and-loop fasteners, adhesive, mechanical fasteners, etc. FIG. 33 shows another application of cover 2400 on a handle 2480 of a hospital bed 182. FIG. 34 shows another application of cover 2400 on a generic handle 2484, e.g., for a desk drawer or cabinet. FIG. 35 shows another application of cover 2400 on a non-round handle 2486. Here, interior 2412 of cover 2400 is shaped to mate with non-round handle 2486. While exterior surface 2416 is shown in a non-round profile in FIG. 35, it does not necessarily have to match the handle. In some examples, cover 2400 may not need to have exterior surface 2416 match the profile shape of high touch surface 2414.

Returning to FIG. 24, some examples of cover 2400 may also include a control system 2490. Control system 2490 may be operatively coupled to light emitter 2420 and may be operative to control operational features of light emitter 2420 such as but not limited to: a duration of illumination, exiting light 2422 color, light intensity, and/or light irradiance. Control system 2490 may include any now known or later developed microcontroller, including a processor, an application specific integrated circuit (ASIC) and the like and/or combinations thereof. Cover 2400 may also include at least one sensor 2492 coupled to control system 2490 to provide feedback to control system 2490. Sensor(s) 2492 may sense any parameter of the control environment of cover 2400, including but not limited to: touch of cover 2400, heat of a user's hand on cover 2400, motion of a user, motion of structure 2415 to which cover 2400 is coupled, temperature, light reception, and/or presence of microorganisms on exterior surface 2416, etc. Sensor(s) may include any now known or later developed sensing devices for the desired parameter(s). Control system 2490 with sensor(s) (and without) may control operation to be continuous or intermittent based on external stimulus, and depending on the application. In one example, sensor(s) 2492 could detect heat/human touch, motion, or light. Sensor(s) 2492 may send the detected information to control system 2490, which may make decisions on exiting light 2422 being emitted through cover 2400, such as the color, intensity, or duration of disinfecting lighting. An example of this type of control may include a human touching a shopping cart handle (e.g., FIGS. 29 and 30) that was previously illuminated with 405 nanometer light. For example, once cover 2400 is touched, the sensor may detect that touch and send information to control system 2490, which then may make the decision to turn cover 2400 to disinfecting white light illumination while in use.

Cover 2400 may be powered through the use of batteries or rechargeable batteries mounted in proximity to the cover. Where rechargeable batteries are employed, they may be recharged, for example, using AC power or perhaps solar panels, where sufficient sunlight is available. Alternatively, cover 2400 may be provided with electrical connectors (not shown) for hardwiring into AC or DC power for applications where this is possible, such as in non-portable products like door handles (e.g., FIG. 35). Wireless or inductive charging may similarly charge or power cover 2400.

FIGS. 36-39 illustrate a flexible cover 3600 comprising a translucent layer 3602 and a flexible light emitting layer 3604. In some examples, the translucent layer 3602 may be cast around a flexible light emitting layer 3604. In some examples, the flexible light emitting layer 3604 may be a flexible printed circuit board comprising one or more LED(s). The translucent layer 3602 may be molded around the flexible light emitting layer 3604 in a liquid or semi-liquid state, and may cure over a threshold amount of time. In some examples, the translucent layer 3602 may be rigid or flexible when cured and may be cast in any shape and/or size. In some examples, the translucent layer 3602 may comprise rubber, silicone, urethane, polysulfide, or any equivalents or combinations thereof. In some examples, when cured, the translucent layer 3602 may comprise a "hardness" on a Shore Hardness Scale between Shore A 10 and Shore A 50. In some examples, when cured, the translucent layer 3602 may comprise a "hardness" on the Shore Hardness Scale between Shore D 50-Shore D 100. In some examples, the translucent layer 3602 may comprise various levels of transparency from completely transparent to almost opaque.

In some examples, the translucent layer 3602 may be cured in a circular (or semi-circular) cross-section, as illustrated in FIG. 37. A flexible light emitter layer 3604 may be similarly flexible with respect to the translucent layer 3602 so that the flexible cover 3600 may conform to a variety of different shapes. In some examples, the flexible light emitting layer 3604 may comprise one or more LEDs 3606 spaced apart such that the flexible light emitter layer 3604 may flex between the one or more LEDs 3606. In some examples, the flexible light emitter layer 3604 may comprise one or more flexible LED strips or layers 3608, such that the flexible light emitter layer 3604 may flex anywhere. The flexible cover 3600 may comprise adhesive on one of the surfaces, enabling it to adhere to a high touch surface.

The example cover 2400 described herein may provide a number of advantages. For example, the cover 2400 may be configured to fit over any existing surface, which eliminates the need to redesign entire products in order to integrate the internally illuminated disinfecting technology. Further, through the use of disinfecting wavelengths between 380-420 nm, e.g., 405 nm light, cover 2400 has been found to effectively reduce the levels of microorganisms on a surface with prolonged exposure, such as bacteria, yeasts, and fungi. Since the germicidal wavelength range disclosed falls within visible light, unlike UV light, it is safe for continuous use around humans and animals, and the exterior surfaces being internally illuminated by these wavelengths may receive continuous disinfection, eliminating intermittent off periods where harmful microorganisms may increase in volume. This ability is beneficial since the surfaces are constantly contacted by multiple humans and need to be disinfected continuously to create a safe environment. Because cover 2400 may be shaped to any shape, it may be applied to any irregularly shape surface, such as hand railings and door handles. For example, any planar high touch surface, either of flat or unequal elevation, may be retrofitted with an internally illuminated disinfecting surface cover 2400. Cover 2400 may also be applied anywhere, even where shadows would normally prevent disinfecting light from reaching a surface. The light wavelengths described herein also do not degrade materials (e.g., plastics) with which it comes into contact.

The terminology used herein is for the purpose of describing examples and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about", "approximately" and "substantially", are not to be limited to the precise value specified. Values identified herein may be varied between +/−10% of the stated value(s) are still function as described. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

An example device may comprise a flexible light emitting layer emitting a light, and a transparent or translucent layer over the flexible light emitting layer, the light traveling through and exiting an exterior surface of the transparent or translucent layer, creating an exiting light, wherein the exiting light exiting the transparent or translucent layer has at least a portion thereof having a wavelength in a range of 380 to 420 nanometers, and wherein the exiting light disinfects the exterior surface of the transparent or translucent layer.

In some examples, the transparent or translucent layer is coupled to a rigid structure.

In some examples, the flexible light emitting layer is coupled flush to the translucent or transparent layer.

In some examples, the flexible light emitting layer includes a flexible substrate and one or more discrete light emitting elements coupled to the flexible substrate.

In some examples, the flexible substrate includes a flexible printed circuit board.

In some examples, each of the one or more discrete light emitting elements includes a light emitting diode (LED).

In some examples, each of the one or more discrete light emitting elements includes a flexible LED.

In some examples, the flexible light emitting layer includes an electroluminescent panel.

In some examples, the flexible light emitting layer includes an organic light emitting diode (OLED).

In some examples, the exiting light includes exclusively light having the wavelength in the range of 380 to 420 nanometers.

In some examples, the exiting light includes at least one additional portion of light above 420 nanometers.

In some examples, the device further comprises a light-converting layer to convert another portion of the light to a wavelength different from the wavelength of the at least the portion of the light emitted from the flexible light emitting layer.

In some examples, the light-converting layer includes one or more of a phosphor, an optical brightener, or a quantum dot.

In some examples, the device further comprises a control system configured to control one or more of a duration of illumination, a light color, a light intensity, or a light irradiance.

In some examples, the device further comprises at least one sensor coupled to the control system. In some examples, the transparent or translucent layer is arranged into a conduit having an elongated hollow interior, and the flexible light emitting layer is within the conduit.

In some examples, the transparent or translucent layer and the conduit are rigid.

In some examples, an interior surface of the conduit has a different cross-sectional shape than an exterior surface of the conduit.

In some examples, the transparent or translucent layer is flexible.

In some examples, the exiting light has an irradiance of no less than 0.01 milliWatts per centimeter squared (0.01 mW/cm$^2$).

An example device for inactivating microorganisms may comprise a flexible light emitting layer emitting a light; and a rigid transparent or translucent conduit having an elongated hollow interior, the light traveling through and exiting an exterior surface of the transparent or translucent layer, creating an exiting light, wherein the exiting light exiting the transparent or translucent conduit has at least a portion thereof having a wavelength in a range of 380 to 420 nanometers, and wherein the exiting light disinfects an exterior surface of the transparent or translucent conduit.

In some examples, the flexible light emitting layer is coupled to an interior surface of the rigid transparent or translucent conduit.

In some examples, the flexible light emitting layer emits a light having a proportion of spectral energy measured in the 380 nm to 420 nm wavelength range between 10% and 44%.

In some examples, the interior surface of the rigid transparent or translucent tube has the same cross-sectional shape as the exterior surface of the rigid transparent or translucent tube.

In some examples, an interior surface of the rigid transparent or translucent conduit has a different cross-sectional shape than an exterior surface of the rigid transparent or translucent conduit. In some examples, the flexible light emitting layer is coupled flush to an interior surface of the rigid translucent or transparent conduit.

An example method may comprise supporting a flexible light emitting layer, the light emitting layer having a first end and a second end, and linearly advancing and rotating a cylindrical mandrel in contact with the flexible light emitting layer while adhering at least a portion of the cylindrical mandrel to flexible light emitting layer to cause the flexible light emitting layer to roll onto the cylindrical mandrel, arranging the flexible light emitting layer into a conduit form, and placing the flexible light emitting layer in the conduit form into a rigid transparent or translucent conduit to form the light emitting device.

In some examples, the adhering includes applying a vacuum across at least a portion of the cylindrical mandrel to cause the flexible light emitting layer to roll onto the cylindrical mandrel.

In some examples, the adhering includes using an adhesive on at least a portion of the cylindrical mandrel to cause the flexible light emitting layer to roll onto the cylindrical mandrel.

In some examples, the method further comprises coupling an exterior surface of the flexible light emitting layer to an interior surface of the rigid transparent or translucent conduit, and removing the cylindrical mandrel.

In some examples, the adhering includes applying a vacuum across at least a portion of the cylindrical mandrel to cause the flexible light emitting layer to roll onto the cylindrical mandrel, and wherein the coupling includes releasing the vacuum and allowing the flexible light emitting layer to expand into and comport to the interior surface of the rigid transparent or translucent conduit.

In some examples, the coupling further includes applying a pressure across at least a portion of an interior surface of the flexible light emitting layer using the cylindrical mandrel to force the exterior surface of the flexible light emitting layer to comport with the interior surface of the rigid transparent or translucent conduit.

In some examples, the method further comprises applying at least one of an adhesive and a sealant to an exterior surface of the flexible light emitting layer prior to placing the flexible light emitting layer in the conduit form into the rigid transparent or translucent conduit.

In some examples, the method further comprises coupling an exterior surface of the flexible light emitting layer to an interior surface of the rigid transparent or translucent conduit, and leaving the cylindrical mandrel.

In some examples, the adhering includes applying a vacuum across at least a portion of the cylindrical mandrel to cause the flexible light emitting layer to roll onto the cylindrical mandrel, and wherein the coupling includes releasing the vacuum and allowing the flexible light emitting layer to expand into and comport with the interior surface of the rigid transparent or translucent conduit.

In some examples, the coupling further includes applying a pressure across at least a portion of an interior surface of the flexible light emitting layer using the cylindrical mandrel to force the exterior surface of the flexible light emitting layer to comport with the interior surface of the rigid transparent or translucent conduit.

In some examples, the method further comprises applying at least one of an adhesive and a sealant to an exterior surface of the flexible light emitting layer prior to placing the flexible light emitting layer in the conduit form into the rigid transparent or translucent conduit.

An example light emitting device that inactivates microorganisms may comprise a flexible light emitting layer emitting a light, and a transparent or translucent layer disposed over the flexible light emitting layer such that the light travels through and exits an exterior surface of the transparent or translucent layer and creates an exiting light, wherein at least a portion of the exiting light comprises a wavelength in a range of 380 to 420 nanometers and comprises a minimum irradiance sufficient to initiate inactivation of microorganisms, and wherein the exiting light disinfects the exterior surface of the transparent or translucent layer.

In some examples, the exiting light continually disinfects the exterior surface of the transparent or translucent layer.

In some examples, an interior surface of the transparent or translucent layer has the same cross-sectional shape as an exterior surface of the transparent or translucent layer.

In some examples, the device further comprises an internal cylinder that the flexible light emitting layer surrounds, wherein the internal cylinder and the flexible light emitting layer are offset from an interior surface of the translucent or transparent layer.

In some examples, the device further comprises one or more endcaps coupled to the internal cylinder and surrounding the translucent or transparent conduit.

An example cover that inactivates microorganisms on a high touch surface may comprise a body having an interior configured to cover at least a portion of the high touch surface and an exterior surface configured to be disinfected, at least an exterior portion of the body being transparent or translucent, and a light emitter operably coupled to the body for emitting a light through the exterior surface, the light exiting the exterior surface having at least a portion thereof having a wavelength in a range of 380 to 420 nanometers.

In some examples, the light emitter includes a flexible light emitter coupled to the interior and facing the exterior surface.

In some examples, the flexible light emitter includes a flexible substrate and one or more light emitting elements.

In some examples, the flexible substrate includes a flexible printed circuit including the one or more light emitting elements thereon.

In some examples, each light emitting element includes a light emitting diode (LED).

In some examples, each light emitting element includes a flexible LED.

In some examples, the flexible light emitter includes an electroluminescent panel.

In some examples, the flexible light emitter includes an organic light emitting diode (OLED) layer.

In some examples, the light emitter is embedded within the body between the interior and the exterior surface.

In some examples, the light emitter includes one or more electroluminescent wires.

In some examples, the light emitter includes one or more light emitting diodes (LEDs).

In some examples, the light emitter is operative to direct the light into the body and out the exterior surface.

In some examples, the light emitter emits light through an edge of the body between the interior and exterior surfaces.

In some examples, the cover further comprises a waveguide within the body for directing the light to the exterior surface.

In some examples, the light emitter includes one or more light emitting diodes (LEDs).

In some examples, the body includes a light-converting layer through which the light travels to convert a portion of the light to a wavelength different from the wavelength of the light emitted from the light emitter.

In some examples, the light-converting layer includes at least one phosphor.

In some examples, the light-converting layer includes at least one optical brightener.

In some examples, the light-converting layer includes at least one quantum dot.

In some examples, the interior is shaped to mate with the high touch surface.

In some examples, the body is tubular and is shaped to mate with the high touch surface.

In some examples, the body is flexible to allow a snap-fit of the interior onto the high touch surface.

In some examples, the interior is C-shaped.

In some examples, the body includes at least two arcuate members configured to be coupled to form a circular body.

In some examples, the light includes exclusively light having the wavelength in the range of 380 to 420 nanometers.

In some examples, the flexible light emitter emits light other than the light having the wavelength in the range of 380 to 420 nanometers.

In some examples, the cover further comprises a control system configured to control at least one: a duration of illumination, light color, light intensity, and light irradiance.

In some examples, the cover further comprises at least one sensor coupled to the control system.

In some examples, the light exiting the exterior surface has an irradiance of at least 0.01 milliWatts per centimeter squared ($mW/cm^2$).

An example light emitting cover that inactivates microorganisms on a high touch surface may comprise a flexible body configured to surround at least a portion of the high touch surface and comprising a surface configured to be disinfected, wherein at least a portion of the flexible body is transparent or translucent, and a light emitter disposed within the flexible body and configured to emit a light through the surface, where at least a portion of the light comprises a wavelength in a range of 380 to 420 nanometers and comprises a minimum irradiance sufficient to initiate inactivation of microorganisms.

In some examples, the light emitting cover may further comprise adhesive disposed thereon for coupling the flexible body to the high touch surface.

In some examples, the light emitter and the flexible body comprise a similar flexibility.

An example light emitting cover for an object that inactivates microorganisms, may comprise a flexible body comprising a first surface configured to surround at least a portion of an object, a second surface configured to be disinfected, wherein at least a portion of the flexible body is transparent or translucent, a flexible light emitting layer disposed within the flexible body and configured to emit a light through the second surface, where a first portion of the light comprises a wavelength of 405 nanometers and comprises an irradiance of at least 0.01 milliWatts per centimeter squared (mW/cm²) at the second surface, and a light-converting layer configured to convert a second portion of the light to a wavelength outside a range of 380 to 420 nanometers.

In some examples, the light-converting layer and the flexible light emitting layer are different layers.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure.

What is claimed is:

1. A light emitting cover for an object that inactivates microorganisms safely for human exposure, the light emitting cover comprising:
    a flexible body comprising:
        a first surface configured to surround at least a portion of an object; and
        a second surface for disinfection and configured to be parallel with the first surface;
        wherein at least a portion of the flexible body is transparent or translucent;
    a flexible light emitting layer disposed within the flexible body and configured to emit a light through the second surface, wherein a first portion of the light comprises a wavelength of 405 nanometers and comprises an irradiance of at least 0.01 milliWatts per centimeter squared (mW/cm²) at the second surface; and
    a light-converting layer configured to convert a second portion of the light to a wavelength outside a range of 380 to 420 nanometers, such that the light through the second surface is a disinfecting light safe for human exposure;
    wherein the flexible light emitting layer is disposed at a first edge of the flexible body and configured to emit light through the flexible body from the first edge, substantially parallel with the second surface, and towards a second edge of the flexible body, wherein the second edge is different from the second surface.

2. The light emitting cover of claim 1, wherein the light-converting layer and the flexible light emitting layer are different layers.

3. A light emitting cover for a first surface that inactivates microorganisms safely for human exposure, the light emitting cover comprising:
    a flexible body configured to surround at least a portion of the first surface and comprising a second surface for disinfection and configured to be parallel with the portion of the first surface, wherein at least a portion of the flexible body is transparent or translucent; and
    a light emitting layer disposed within the flexible body and configured to emit:
        a first portion of light comprising:
            a wavelength in a range of 380 to 420 nanometers (nm); and
            a minimum irradiance sufficient to initiate inactivation of microorganisms on the second surface; and
        a second portion of light comprising a wavelength greater than 450 nm;
    wherein the light emitting layer is disposed at a first edge of the flexible body and configured to emit light through the flexible body from the first edge, substantially parallel with the second surface, and towards a second edge of the flexible body, wherein the second edge is different from the second surface.

4. The light emitting cover of claim 3, wherein the light emitting layer includes a flexible light emitting layer coupled to an interior surface of the flexible body and facing the second surface of the flexible body.

5. The light emitting cover of claim 4, wherein the flexible light emitting layer includes a flexible printed circuit board and one or more of a light emitting diode (LED) or a flexible LED.

6. The light emitting cover of claim 4, wherein the flexible light emitting layer includes one or more of an electroluminescent panel or an organic light emitting diode (OLED) layer.

7. The light emitting cover of claim 3, wherein the light emitting layer includes electroluminescent wires.

8. The light emitting cover of claim 3, wherein the light emitting layer is configured to direct the light into the flexible body and out the second surface.

9. The light emitting cover of claim 3, further comprising a waveguide within the flexible body for directing the light to the second surface.

10. The light emitting cover of claim 3, wherein the light emitting layer comprises a light-converting layer configured to convert the first portion of the light to the second portion of light.

11. The light emitting cover of claim 10, wherein the light-converting layer includes one or more of a phosphor, an optical brightener, or a quantum dot.

12. The light emitting cover of claim 3, further comprising a control system configured to control a light color.

13. The light emitting cover of claim 3, wherein the minimum irradiance is at least 0.01 milliWatts per centimeter squared (mW/cm²) at the second surface.

14. The light emitting cover of claim 3, wherein the first portion of light comprises at least 20% of a spectral energy of a total light emitted by the light emitting layer.

15. The light emitting cover of claim 3, further comprising:
    a sensor operable to detect a frequency with which the second surface is physically touched; and
    a control system operable to adjust, based on the detected frequency with which the second surface is physically touched, the irradiance of the first portion of light on the second surface.

16. A light emitting cover for an object that inactivates microorganisms safely for human exposure, the light emitting cover comprising:
    a body comprising:
        an interior surface configured to conform to at least a portion of a surface of the object; and
        an exterior surface for disinfection and configured to be parallel with the interior surface;
        wherein at least a portion of the body is transparent or translucent; and
    a light emitting layer operably coupled to the body and configured to direct a light through the body substantially parallel with the exterior surface, wherein at least a portion of the light comprises:
    a wavelength in a range of 380 to 420 nanometers; and
    a minimum irradiance sufficient to initiate inactivation of microorganisms on the exterior surface;
    wherein the light emitting layer is disposed at a first edge of the body and configured to emit light through the body from the first edge, substantially parallel with the exterior surface, and towards a second edge of the body, wherein the second edge is different from the exterior surface.

17. The light emitting cover of claim 16, wherein the light emitting layer and the body comprise a similar flexibility.

18. The light emitting cover of claim 16, wherein the light directed through the body comprises a second portion of light comprising a wavelength greater than 450 nm and wherein the light emitting layer is configured to cause the portion of the light comprising the wavelength in the range of 380 to 420 nanometers to be between 10% and 44% of a spectral energy of the light directed through the body.

19. The light emitting cover of claim 16, wherein the body comprises at least two arcuate members configured to be coupled to form a circular body.

20. The light emitting cover of claim 16, further comprising a waveguide disposed within the body for directing the light to the exterior surface.

* * * * *